(12) United States Patent
Rubinsky et al.

(10) Patent No.: US 10,668,208 B2
(45) Date of Patent: *Jun. 2, 2020

(54) BALLOON CATHETER METHOD FOR REDUCING RESTENOSIS VIA IRREVERSIBLE ELECTROPORATION

(71) Applicants: THE REGENTS OF THE UNIVERSITY OF CALIFORNIA, Oakland, CA (US); ANGIODYNAMICS, INC., Latham, NY (US)

(72) Inventors: Boris Rubinsky, El Cerrito, CA (US); Elad Maor, Berkeley, CA (US); Antoni Ivorra, Berkeley, CA (US); James J. Mitchell, Ballston Spa, NY (US); William C. Hamilton, Queensbury, NY (US)

(73) Assignees: THE REGENTS OF THE UNIVERSITY OF CALIFORNIA, Oakland, CA (US); ANGIODYNAMICS, INC., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/988,408

(22) Filed: May 24, 2018

(65) Prior Publication Data
US 2019/0160222 A1    May 30, 2019

Related U.S. Application Data

(63) Continuation of application No. 14/313,647, filed on Jun. 24, 2014, now Pat. No. 10,010,666, which is a
(Continued)

(51) Int. Cl.
*A61N 1/32* (2006.01)
*A61B 18/14* (2006.01)
(Continued)

(52) U.S. Cl.
CPC .............. *A61M 5/14* (2013.01); *A61B 18/14* (2013.01); *A61B 18/1492* (2013.01);
(Continued)

(58) Field of Classification Search
CPC . A61B 17/0057; A61B 18/14; A61B 18/1492; A61B 2018/00214;
(Continued)

(56) References Cited

U.S. PATENT DOCUMENTS

| 4,822,470 A  * | 4/1989 | Chang .................... C12M 35/02 |
| | | 435/173.6 |
| 10,010,666 B2 * | 7/2018 | Rubinsky ........... A61B 18/1492 |

(Continued)

*Primary Examiner* — William R Carpenter
*Assistant Examiner* — Larry R. Wilson
(74) *Attorney, Agent, or Firm* — Bozicevic, Field & Francis LLP; Karl Bozicevic

(57) ABSTRACT

Restenosis or neointimal formation may occur following angioplasty or other trauma to an artery such as by-pass surgery. This presents a major clinical problem which narrows the artery. The invention provides a balloon catheter with a particular electrode configuration. Also provided is a method whereby vascular cells in the area of the artery subjected to the trauma are subjected to irreversible electroporation which is a non-thermal, non-pharmaceutical method of applying electrical pulses to the cells so that substantially all of the cells in the area are ablated while leaving the structure of the vessel in place and substantially unharmed due to the non-thermal nature of the procedure.

9 Claims, 34 Drawing Sheets

Related U.S. Application Data continuation of application No. 12/413,357, filed on Mar. 27, 2009, now abandoned.

(60) Provisional application No. 61/156,368, filed on Feb. 27, 2009, provisional application No. 61/040,110, filed on Mar. 27, 2008.

(51) Int. Cl.
*A61M 5/14* (2006.01)
*A61B 17/22* (2006.01)
*A61B 18/00* (2006.01)

(52) U.S. Cl.
CPC .... *A61N 1/327* (2013.01); *A61B 2017/22038* (2013.01); *A61B 2018/0022* (2013.01); *A61B 2018/0041* (2013.01); *A61B 2018/00166* (2013.01); *A61B 2018/00214* (2013.01); *A61B 2018/00613* (2013.01); *A61B 2018/1435* (2013.01)

(58) Field of Classification Search
CPC .. A61B 2018/0022; A61B 2018/00613; A61B 2018/1435; A61F 2/01; A61F 2/013; A61F 2/82; A61F 2/88; A61F 2/885; A61F 2/90; A61F 2002/016; A61F 2230/0091; A61F 2250/0048; A61F 2210/0014; A61M 5/14; A61M 25/0074; A61M 25/04; A61N 1/327
See application file for complete search history.

(56) References Cited

U.S. PATENT DOCUMENTS

2001/0044596 A1* 11/2001 Jaafar .................. A61N 1/327
604/103.01
2007/0282407 A1* 12/2007 Demarais ................ A61F 7/123
607/113

* cited by examiner

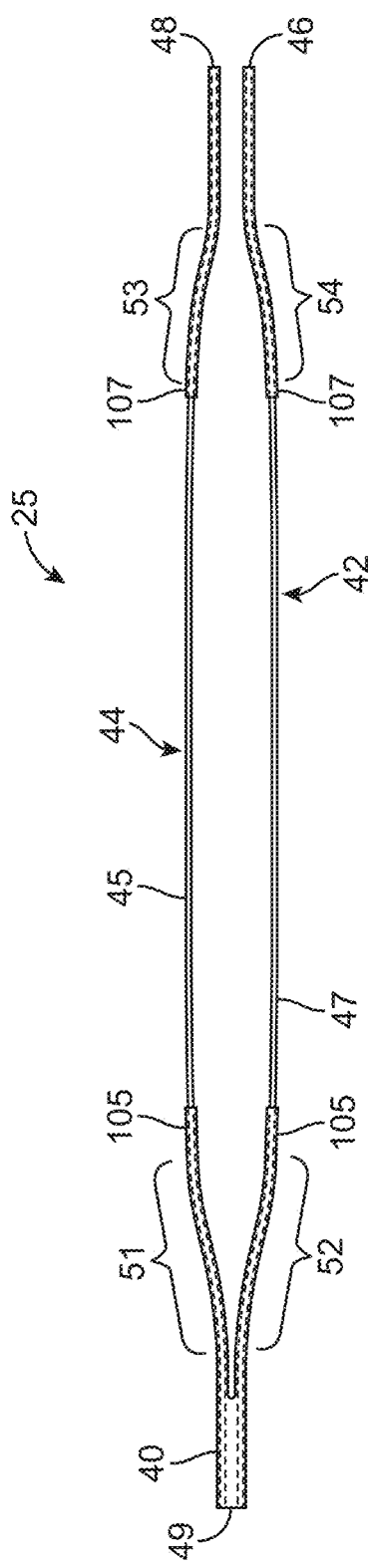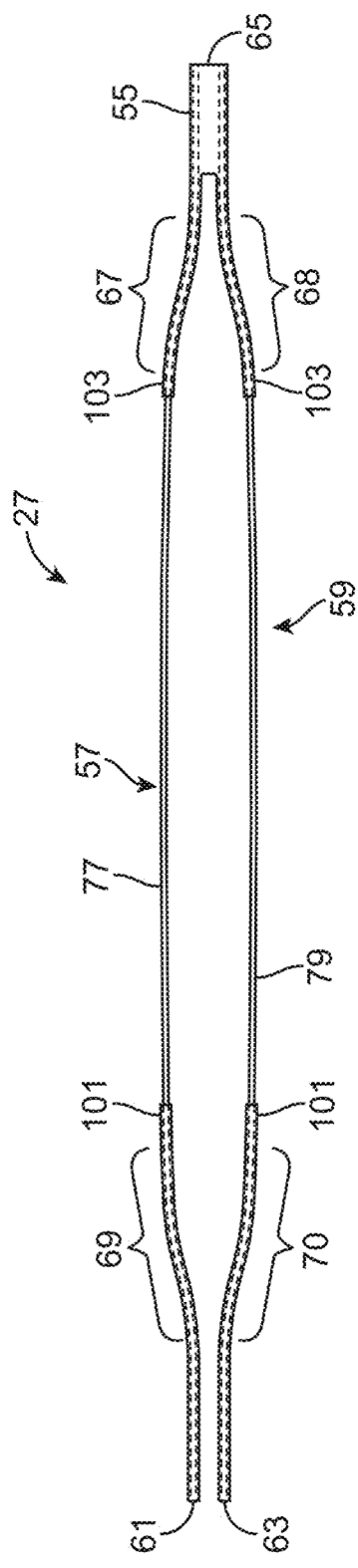

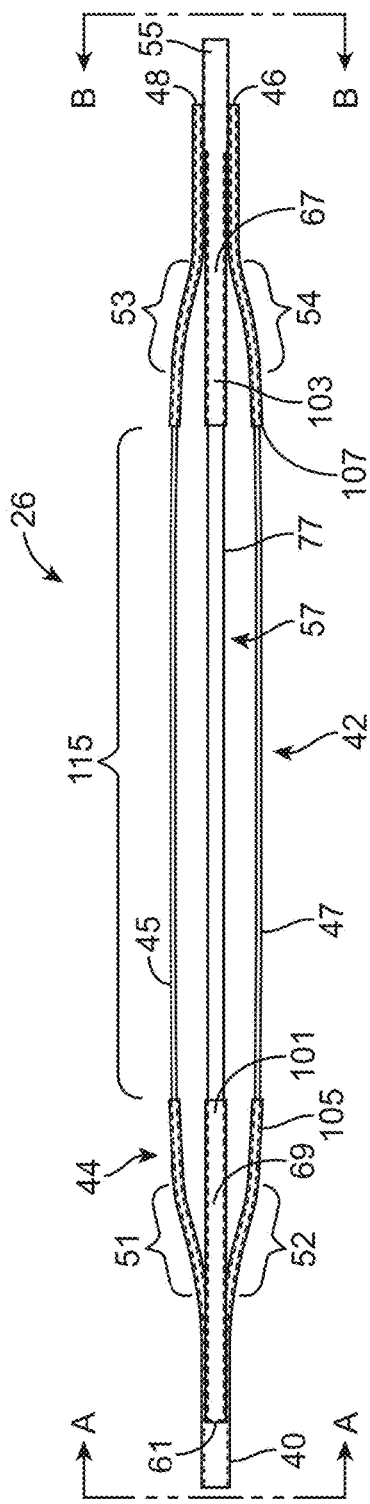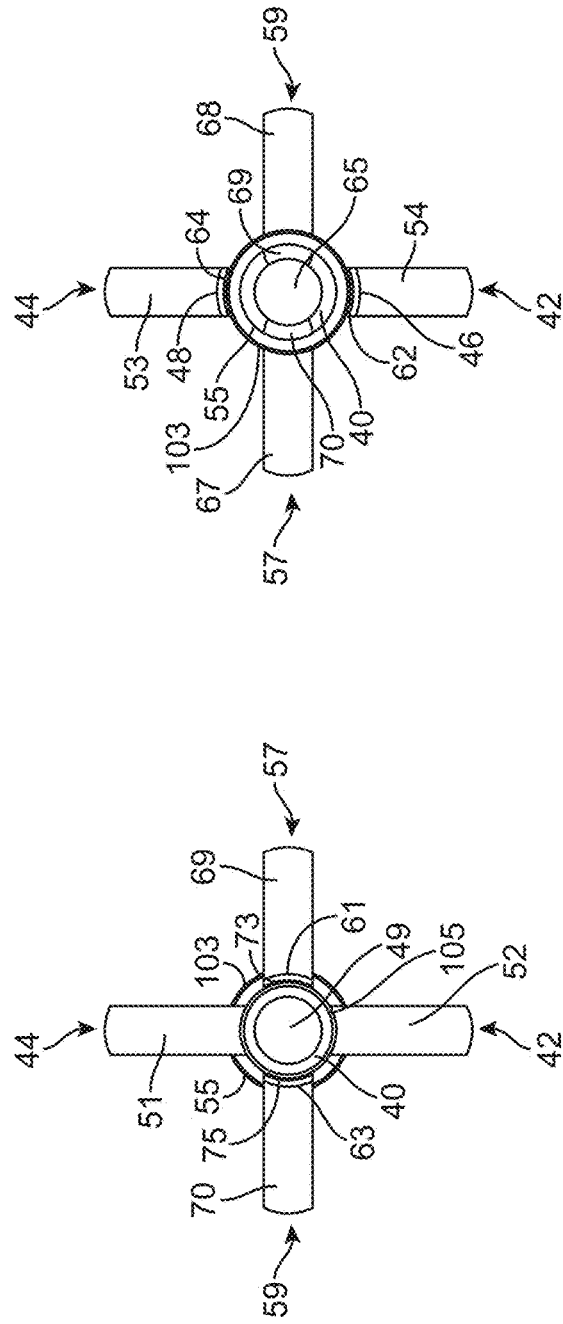
FIG. 4A
FIG. 4C
FIG. 4B

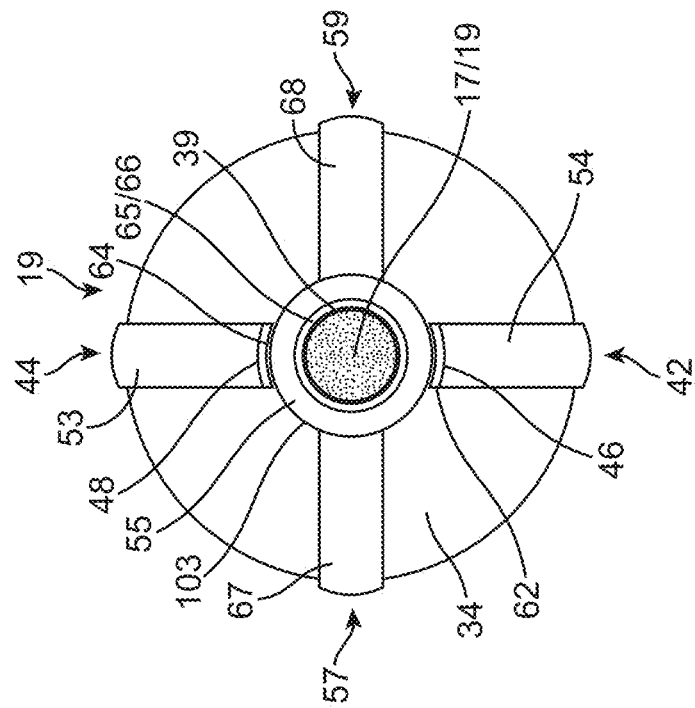
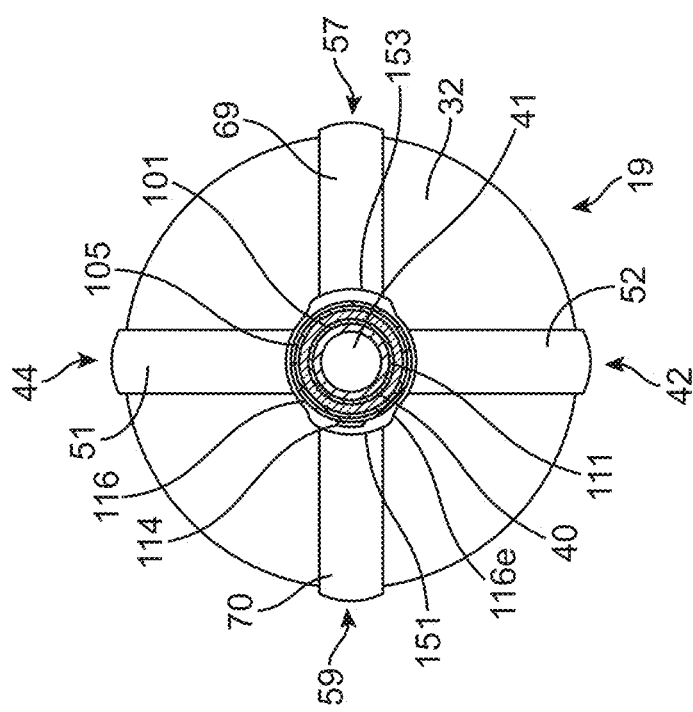
FIG. 7B
FIG. 7A

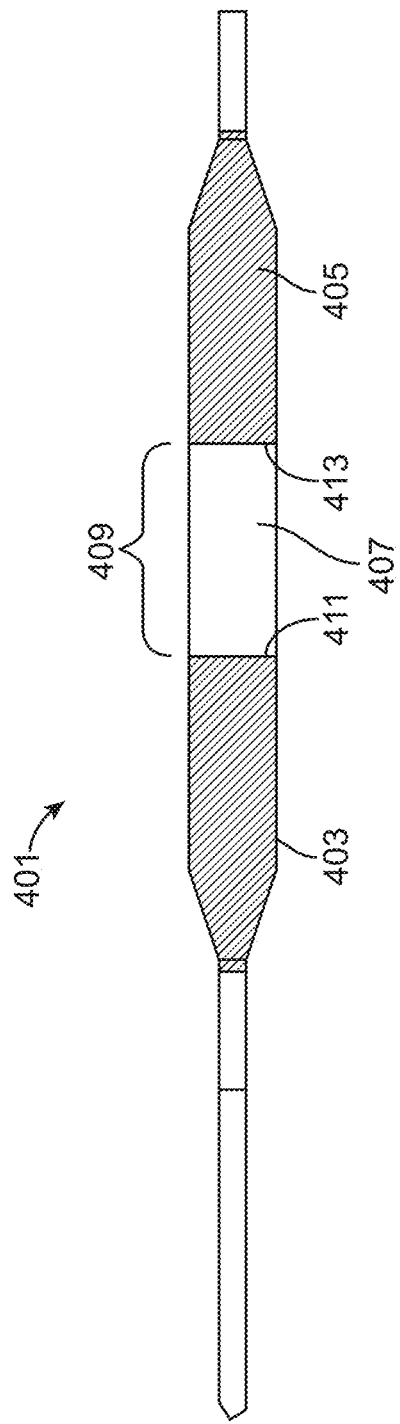
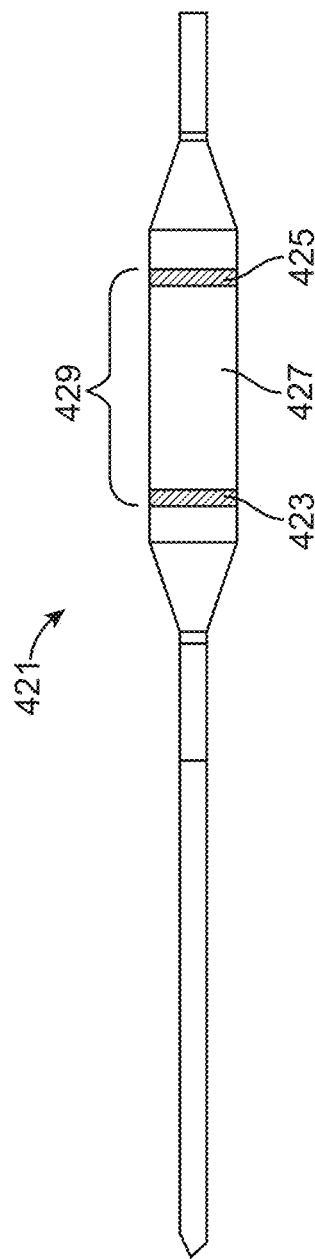
FIG. 18A
FIG. 18B

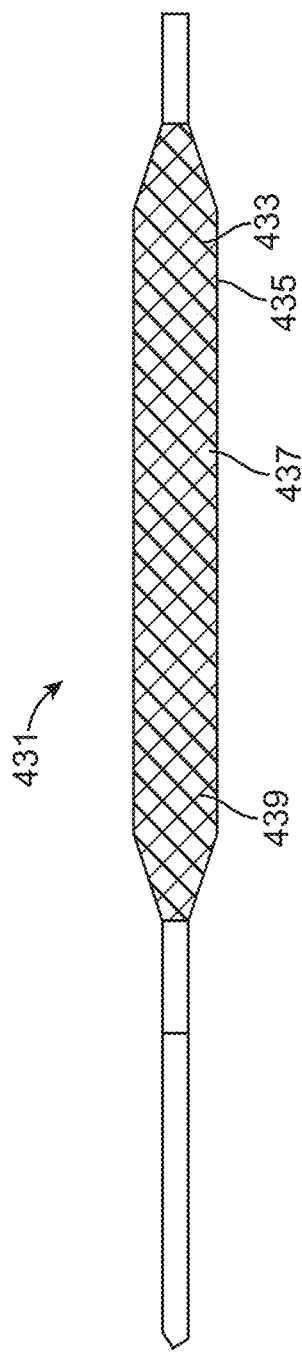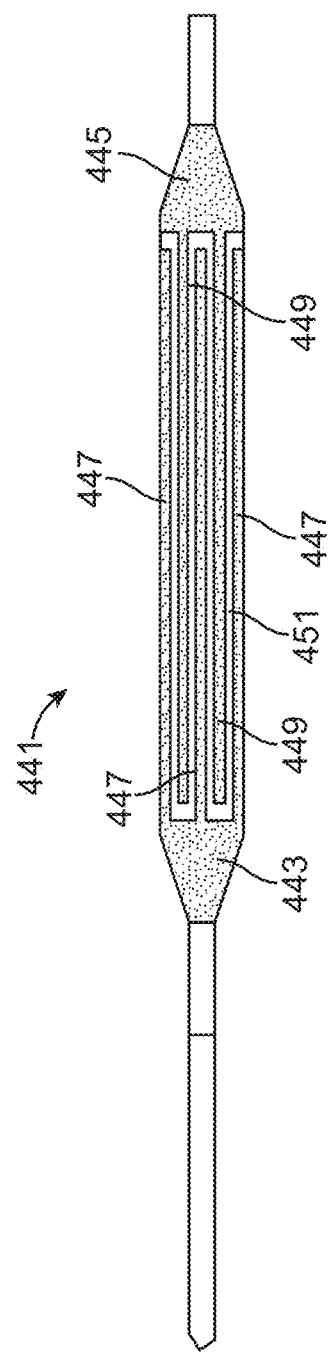

Morphometric analysis of experiment slides

| Animal# | Intervention | Tunica media area (mm2) | Neointima area (mm2) | Lumen area (mm2) | Neointima/Media ratio | Neointima/Media average ratio* |
|---|---|---|---|---|---|---|
| 1 | Intimal damage & successful IRE | 0.17 | 0.18 | 0.27 | 1.07 | 0.57±0.4 |
| 2 | Intimal damage & successful IRE | 0.08 | 0.03 | 0.32 | 0.38 | |
| 3 | Intimal damage & successful IRE | 0.16 | 0.04 | 0.31 | 0.28 | |
| 4 | Intimal damage & failed IRE ** | 0.08 | 0.21 | 0.05 | 2.69 | |
| 5 | Intimal damage alone | 0.17 | 0.17 | 0.30 | 0.99 | 1.67±1.0 |
| 6 | Intimal damage alone | 0.11 | 0.11 | 0.30 | 1.01 | |
| 7 | Intimal damage alone | 0.11 | 0.17 | 0.35 | 1.49 | |
| 8 | Intimal damage alone | 0.12 | 0.38 | 0.25 | 3.19 | |

*P=0.06
**Unsuccessful IRE (See text)

FIG. 23

| Group | Electric Field [V/cm] | # Pulses | Frequency [Hz] | # Animals |
|---|---|---|---|---|
| 1 | 3500 | 10 | 10 | 5 |
| 2 | 1750 | 10 | 10 | 4 |
| 3 | 875 | 10 | 10 | 4 |
| 4 | 437.5 | 10 | 10 | 4 |
| 5 | 1750 | 45 | 4 | 4 |
| 6 | 875 | 45 | 4 | 4 |
| 7 | 1750 | 90 | 4 | 4 |
| 8 | 875 | 90 | 4 | 4 |

FIG. 24

| | 3500X10 (Group 1) | | | 1750X10 (Group 2) | | | 875X10 (Group 3) | | | 437.5X10 (Group 4) | | |
|---|---|---|---|---|---|---|---|---|---|---|---|---|
| | Control | IRE | % | Control | IRE | % | Control | IRE | % | Control | IRE | % |
| Cell Number | 208±40 | 24±34 | 11 | 214±38 | 167±66 | 78 | 196±30 | 208±58 | 106 | 213±38 | 209±25 | 98 |
| Concentration | 1±0.2 | 0.2±0.2 | 16 | 1±0.2 | 0.9±0.2 | 88 | 1±0.2 | 0.8±0.3 | 83 | 1.3±0.2 | 1.3±0.2 | 101 |
| Area | 2.2±0.4 | 1.8±0.3 | 81 | 2.1±0.2 | 1.8±0.3 | 86 | 2±0.4 | 2.8±0.4 | 136 | 1.7±0.4 | 1.6±0.3 | 98 |
| Thickness | 59±8 | 45±10 | 75 | 57±3 | 54±5 | 94 | 58±7 | 61±9 | 105 | 60±6 | 61±9 | 102 |

FIG. 25

|  | 1750X45 (Group 5) | | | 875X45 (Group 6) | | | 1750X90 (Group 7) | | | 875X90 (Group 8) | | |
|---|---|---|---|---|---|---|---|---|---|---|---|---|
|  | Control | IRE | % | Control | IRE | % | Control | IRE | % | Control | IRE | % |
| Cell Number | 204±20 | 30±33 | 14 | 230±53 | 85±66 | 37 | 213±33 | 13±21 | 6 | 236±61 | 49±40 | 21 |
| Concentration | 1.5±0.1 | 0.3±0.3 | 18 | 1.6±0.2 | 0.6±0.4 | 27 | 1.5±0.2 | 0.1±0.2 | 7 | 1.6±0.2 | 0.4±0.3 | 39 |
| Area | 1.3±0.1 | 0.97±0.2 | 73 | 1.4±0.2 | 1.3±0.2 | 70 | 1.5±0.3 | 1.3±0.2 | 77 | 1.5±0.2 | 1.1±0.2 | 88 |
| Thickness | 52±3 | 35±6 | 67 | 52±4 | 47±8 | 70 | 51±6 | 37±4 | 73 | 50±4 | 35±6 | 90 |

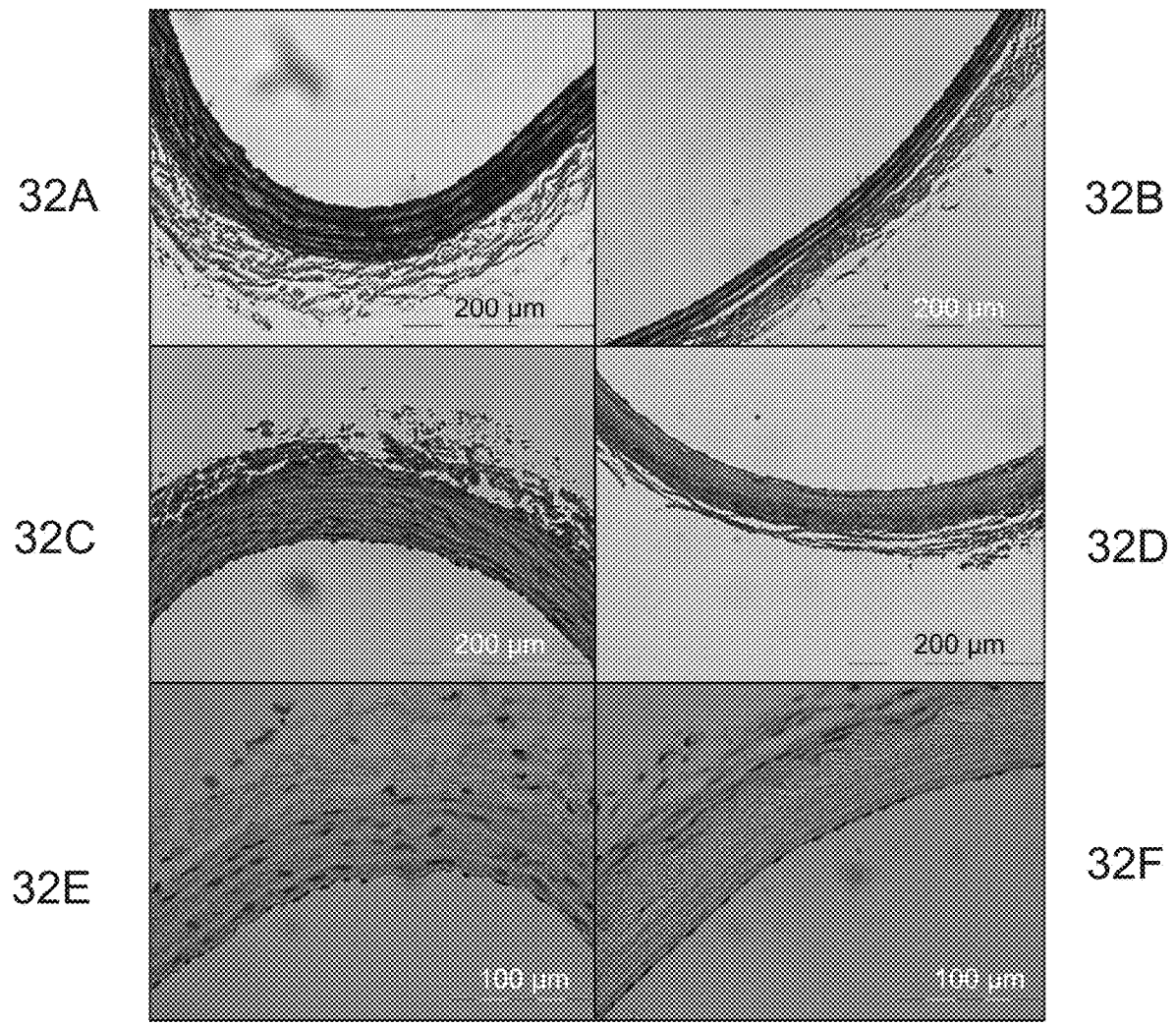
FIG. 32A-F

BALLOON CATHETER METHOD FOR REDUCING RESTENOSIS VIA IRREVERSIBLE ELECTROPORATION

FIELD OF THE INVENTION

The present invention relates to a medical device and method for the prevention of vascular re-stenosis using electroporation. More particularly, the present invention relates to a balloon catheter device with electrodes for electroporating the inner wall of a vascular structure to prevent re-stenosis.

BACKGROUND OF THE INVENTION

Catheters, and more particularly, balloon catheters have been used to treat stenosis of a vascular or other anatomical tubular structure. In one such procedure, called percutaneous transluminal angioplasty or PTA, a balloon catheter is inserted into a vessel and advanced to the site of the stenosis or lesion where the balloon is inflated against the lesion. Pressure applied to the stenosis by the surface of inflated balloon compresses the lesion, pushing it radially outward and widening or restoring the luminal diameter of the vessel. Various forms of PTA have been used to treat peripheral arterial stenosis, coronary lesions and other non-vascular tubular structures such as biliary ducts.

Notwithstanding the importance of PTA procedures in restoring normal blood flow to an anatomical region, one problem associated with PTA procedures is the undesired re-growth of the lesion, commonly known as re-stenosis. Re-stenosis, a re-narrowing of the vessel lumen, usually occurs within three to six months after the angioplasty procedure. Studies have demonstrated a re-stenosis rate after angioplasty in up to 50% of patients treated. Although the use of stents has reduced the re-stenosis rate to approximately 30% of the procedures, re-stenosis remains a significant clinical problem, particularly for those patients whose general health is not conducive to repeat interventional procedures.

The main cause of re-stenosis following angioplasty procedures is due to vessel wall trauma created during the procedure. Evidence has shown that scar tissue forms as endothelial cells that line the inner wall of the blood vessel regenerate in response to the vessel wall injury created during angioplasty. An overgrowth of endothelial cells triggered by the trauma leads to a re-narrowing of the vessel and eventual re-stenosis of the treated area. Cutting wire balloon catheters, also known in the art, have been used to "score" a stenotic lesion in a more controlled, precise manner. Although it is contemplated that scoring a lesion will lead to less procedural vessel trauma, endothelial cell re-growth and re-stenosis, to date there are no studies that effectively demonstrate this.

Recently, advances in stent technology have included drug-eluting stents which are intended to reduce the occurrence of re-stenosis even further. These types of stents are coated with a drug designed to suppress growth of scar tissue along the inner vessel wall over an extended period of time. The drug is slowly released or eluted, thus reducing the occurrence and extent of re-stenosis when compared with bare stents. Although shown to be effective in further reducing re-stenosis, there are several known problems with drug-eluting stents including an increased risk in some patient populations of localized blood clots after the drug has been completely eluted, usually after six or more months. Clot formation in the coronary system can lead to heart attack and death. Other problems include stent fracture and other known risks associated with long-term implants.

Therefore, it is desirable to provide a device and method for the prevention of re-stenosis associated with primary angioplasty and/or stenting procedures that is safe, easy and does not require placement of a stent.

SUMMARY OF THE INVENTION

A catheter device for insertion into a vessel which device is used for reducing neotima or reducing the occurrence of restenosis is disclosed. The present invention can utilize basic structural configurations of a balloon catheter device modified to incorporate electrodes which can be electrically connected to a power source for the administration of electrical pulses which can provide for irreversible electroporation. Thus, a device of the invention includes a basic balloon catheter configuration having a first electrode positioned at a distal end of the catheter. A second electrode is positioned at a point relative to the first electrode so as to allow electrical current to flow between the first and second electrodes and through vascular tissue. The device includes a power source and electrical connections from the power source to the electrodes. The power source provides electrical pulses to the electrodes for durations, voltages, current amounts and combinations thereof so as to provide sufficient electrical flow to substantially all of the vascular cells in the area of an artery (which has been subjected to trauma) to irreversible electroporation (IRE) which is preferably done before neointima occurs.

In an aspect of the invention the catheter is a balloon catheter and the electrodes may encircle the catheter in a spiral configuration.

In one embodiment the first and second electrodes are designed for use following a by-pass surgery or alternatively are designed for use following angioplasty with a balloon angioplasty device which may be the same device to which the electrodes are connected.

The system of the invention may be comprised of two separate catheter devices wherein a first catheter device is a balloon catheter which is used for carrying out balloon angioplasty and a second catheter which is specific for use in the IRE.

The system of the invention is designed for use wherein the IRE is carried out using a voltage, and a current within defined ranges over a defined period of time and in the absence of drug being delivered into the vascular cells.

In another embodiment of the invention the device comprises an electrical power source which provides electrical pulses which provide voltage, current and are provided for a duration so as to avoid thermal damage to a target area and surrounding tissues while obtaining the IRE on the target area.

In another embodiment of the device the power source is designed to emit pulses wherein the pulses have a duration from 50 to 200 microseconds and the device may be designed for carrying out the IRE immediately following balloon angioplasty or alternatively the IRE may be carried out immediately prior to balloon angioplastly.

The system of the invention includes an electrical power source which is specifically designed for carrying out the IRE so as to reduce restenosis or neointimal and avoid thermal damages. The power source may be designed to deliver a range of different voltages, currents and duration of pulses as well as number of pulses. The system may be designed to provide for pulse durations from about 50 to 200 microseconds and may administer a current in a range of from about 2,000 V/cm to about 6,000 V/cm. The power source may provide between 2 and 25 pulses upon activation and may be designed to provide a specific number of pulses which are at a specific known duration and with a specific amount of current. For example, the power source may be designed upon activation to provide 10 pulses for 100 microseconds each providing a current of 3,800 V/cm±50%, ±25%, ±10%, ±5%.

A method of reducing, attenuating or eliminating the intimal formation on a patient that has undergone a surgical procedure in a target area of an artery is disclosed. The method first involves diagnosing a subject which may be a human subject suffering from coronary artery disease and specifically identifying a target area of an artery in the subject which is partially blocked by plaque. A procedure is performed whereby blockage in the target area is moved or removed from the artery so as to increase blood flow through the target area of the artery. This procedure can be balloon angioplasty whereby the plaque is forced away from the area of flow or can involve by-pass surgery whereby the blocked area of the artery is completely removed.

After the procedure is carried out vascular cells in the area subjected to trauma by the angioplasty or surgery are subjected to irreversible electroporation (IRE). The IRE may be carried out (1) before, (2) at substantially the same time, or (3) just after the procedure (e.g. angioplasty) is carried out, but is carried out before restenosis occurs to obtain the best results. The IRE may be carried out by the use of electrodes which are present on or near the balloon portion of the balloon catheter used in the angioplasty. The IRE is carried out using a voltage and current within defined ranges over a defined period of time. Further, the IRE is carried out in the absence of a drug being delivered to the vascular cells in a manner which would effect the growth of the cells.

The IRE is not carried out in order to provide for reversible electroporation of substantially all of the cells. Reversible electroporation is carried out when the pores of the cells are temporarily opened and after the procedure go back to normal size and the cells survive. Others carry out electroporation in a manner so as to prevent excessive cell lysing (see U.S. Pat. Nos. 6,865,416 and 6,342,247). With irreversible electroporation the pores of the cells are opened and are opened to a degree that they do not return to normal size and the cells die, so excessive lysing of cells is desired. Thus, irreversible electroporation requires more voltage, current or time in order to obtain the desired result as compared to reversible electroporation. The amount of current used and the time it is applied must be controlled in accordance with the invention in order to avoid thermal damage. The result sought per the present invention is to have substantially all of the vascular cells of the targeted area of the artery ablated or killed but to not raise the temperature of that area sufficiently to cause thermal damage and denature proteins. By avoiding thermal damage the structure of the artery and surrounding tissue remains in place. However, due to the irreversible electroporation the vascular cells are killed and as such do not form scar tissue (neointimal) in the area thereby reducing or avoiding restenosis.

The methodology of the invention may involve carrying out the IRE at substantially the same time the balloon angioplasty or by-pass surgery is carried out. It would be possible to carry out the IRE prior to angioplasty or by-pass surgery or other trauma event or carry out the IRE at substantially immediately after the balloon angioplasty or by-pass surgery or other trauma event is carried out. The timing of carrying out the IRE relative to the timing of the trauma event is important in order to avoid the occurrence of restenosis and avoid as much as possible the artery being blocked with respect to blood flow.

In addition to the timing of the IRE the parameters of the IRE in terms of voltage/current/pulse duration are important. These parameters are important so as to go beyond reversible electroporation and obtaining irreversible electroporation. Further, the parameters are important so as to avoid thermal damage. It is undesirable to heat the area in that too much heat can cause denaturation of the proteins. Denaturation of the proteins results in breakdown of those proteins which thereafter can result in structural breakdown of the vessel which is undesirable. Thus, the method of the invention is intended to go beyond reversible electroporation to obtain irreversible electroporation but not obtain thermal damage.

BRIEF DESCRIPTION OF THE DRAWINGS

FIG. 3A is a plan view of a first longitudinal electrode of the electrode assembly.

FIG. 3B is a plan view of a second longitudinal electrode of the electrode assembly.

FIG. 4A illustrates a plan view of the electrode assembly comprising the first and second longitudinal electrodes.

FIG. 4B depicts end views of the electrode assembly taken from lines A-A of FIG. 4A.

FIG. 4C is a view taken from the lines of B-B of FIG. 4A.

FIG. 7A illustrates an end view of the balloon and electrode assembly taken along lines C-C and D-D of FIG. 1A.

FIG. 7B is a 90° rotated version of FIG. 7A.

FIG. 18A shows another embodiment of the electrode configurations of the electrode balloon catheter of the current invention.

FIG. 18B shows another embodiment of the electrode configurations of the electrode balloon catheter of the current invention.

FIG. 18C shows another embodiment of the electrode configurations of the electrode balloon catheter of the current invention.

FIG. 18D shows another embodiment of the electrode configurations of the electrode balloon catheter of the current invention.

FIG. 19A shows the clamp is comprised of two printed circuit boards (1.5 mm thickness) with disk electrodes (diameter=5 mm) made of copper (70 microns thickness) plated with gold (manufacturing process by Sierra Proto Express, Sunnyvale, Calif., USA).

FIG. 19B shows a photograph where the clamp is used for clamping the carotid artery, where the distance between electrodes was approximately 0.3 mm

FIG. 23 is a Table showing results obtained on 8 animal models of the device used in Example I.

FIG. 24 is a Table showing the eight different electroporation parameters used in this study of Example 2. Groups differ in the magnitude of the applied electric field, the number of the pulses and their frequency. All pulses were square pulses, 100 μs in length. Frequency of 10 Hz was used for the 10-pulse protocols, and was reduced to 4 Hz for 45 or 90 pulse protocols to prevent significant heating.

FIG. 25 is a Table showing data of the four different 10-pulse protocols of Example 2. All data are shown as average with standard deviation, and include the percentage of IRE values compared with control. Cell number is the average number of VSMC nuclei identified in the Tunica Media. Concentration is the ratio between the number of cells and the area of the Tunica Media ($10^{-3}$ mm$^2$). Area is the total area of the Tunica Media ($10^{-1}$ mm$^2$), and the thickness is the thickness of the Tunica Media based on five different measurements in each section in micrometers.

FIG. 26 is a Table showing data for the four different protocols with more than 10 pulses. All data are shown in the same manner as in FIG. 25 of Example 2.

FIG. 32A is an actual photograph of tissues subjected to histology staining of Example 2.

FIG. 32B is an actual photograph of tissues subjected to histology staining of Example 2.

FIG. 32C is an actual photograph of tissues subjected to histology staining of Example 2.

FIG. 32D is an actual photograph of tissues subjected to histology staining of Example 2.

FIG. 32E is an actual photograph of tissues subjected to histology staining of Example 2.

FIG. 32F is an actual photograph of tissues subjected to histology staining of Example 2.

FIGS. 32A, 32B, 32C, 32D, 32E and 32F are six actual photographs of tissues subjected to histology staining of Example 2. Left column 32A, 32C, and 32E show control arteries and right column 32B, 32D and 32F show IRE-treated arteries. Top row (32A and 32B)—EVG stain showing undamaged elastic fibers in IRE-treated arteries (elastic Van Gieson, ×40). Middle row (32C and 32D)—Masson Trichrome stain showing mild fibrosis in the perivascular area with dominance of collagen fibers in the Tunica Media of the IRE-treated Arteries (Masson Trichrome, ×40). Lower row—(32E and 32F) Negative staining of both arteries with CD34 antibodies at higher magnification (×60). Note the similar morphology and distribution of the endothelial cells.

DETAILED DESCRIPTION OF THE INVENTION

Figure 1A:
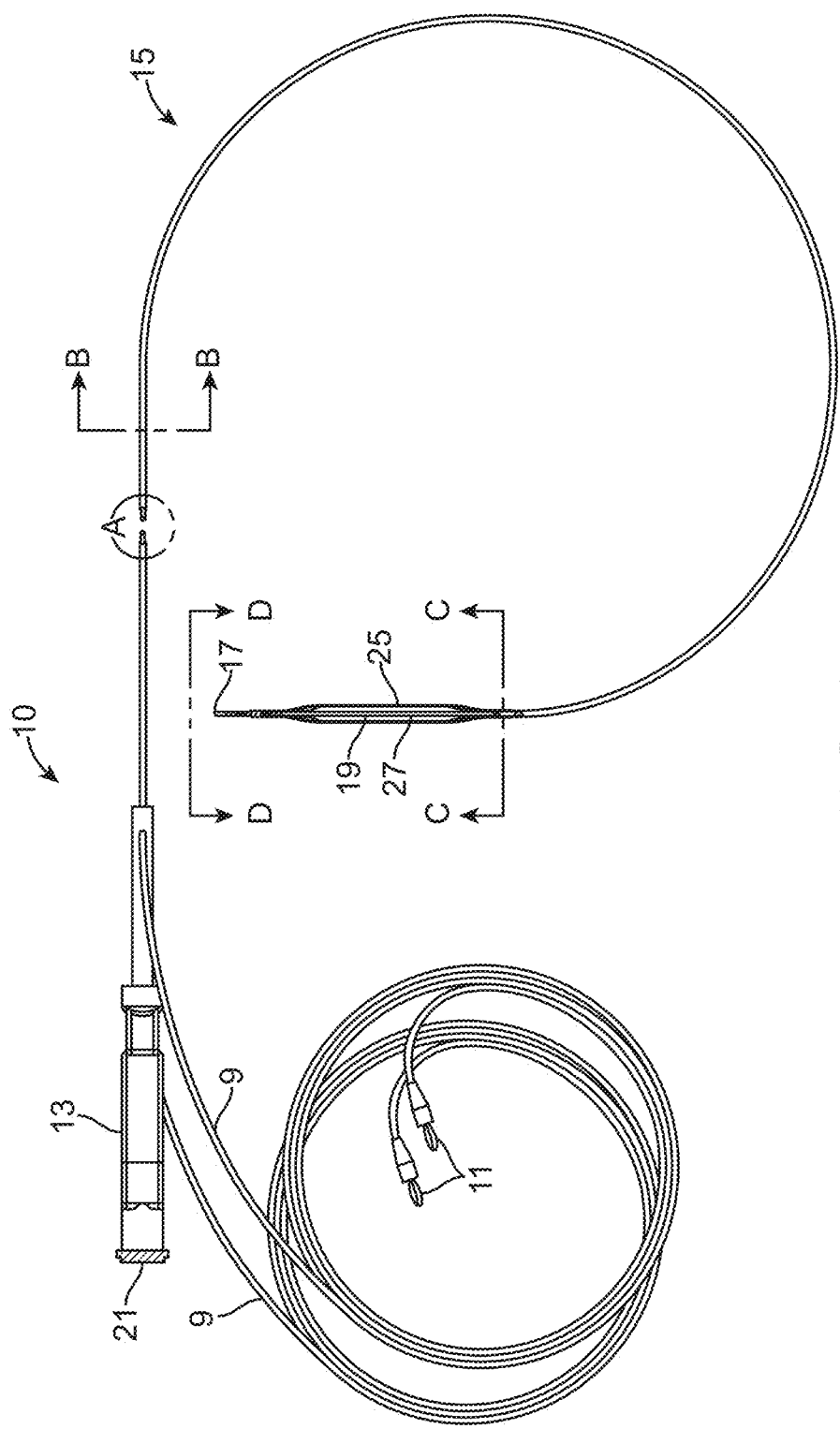
FIG. 1A is a plan view of an embodiment of an electroporation balloon catheter of the present invention with a balloon and electrode assembly at the distal portion of the catheter.

Before the present method of treating restenosis and device and system used for same are described, it is to be understood that this invention is not limited to particular devices or method steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a target area" includes a plurality of such target area and reference to "restenosis" includes reference to one or more areas of restenosis and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Electroporation

Electroporation is defined as a phenomenon that makes cell membranes permeable by exposing them to certain electric pulses. As a function of the electrical parameters, electroporation pulses can have two different effects on the permeability of the cell membrane. The permeabilization of the cell membrane can be reversible or irreversible as a function of the electrical parameters used. Reversible electroporation is the process by which the cellular membranes are made temporarily permeable. The cell membrane will reseal a certain time after the pulses cease, and the cell will survive. Reversible electroporation is most commonly used for the introduction of therapeutic or genetic material into the cell. Irreversible electroporation, also creates pores in the cell membrane but these pores do not reseal, resulting in cell death.

Irreversible electroporation has recently been discovered as a viable alternative for the ablation of undesired tissue. See, in particular, PCT Application No. PCT/US04/43477, filed Dec. 21, 2004. An important advantage of irreversible electroporation, as described in the above reference application, is that the undesired tissue can be destroyed without creating a thermal effect. When tissue is ablated with thermal effects, not only are the cells destroyed, but the elastin, collagen and other extra-cellular matrix components (tissue scaffolding) of blood vessels are also destroyed. This thermal mode of damage detrimentally affects the tissue, that is, it destroys the vasculature structure and bile ducts, and produces collateral damage.

Irreversible and reversible electroporation without thermal effect to ablate tissue offers many advantages. One advantage is that it does not result in thermal damage to target tissue or other tissue surrounding the target tissue. Another advantage is that it only ablates cells and does not damage blood vessel structure itself. Accordingly, irreversible electroporation may be used to treat the inner wall of a blood vessel during or immediately following balloon angioplasty to prevent the re-growth of endothelial cells.

Human arteries and veins are comprised of three layers; the intima which is the thinnest and innermost layer; the media which is the thickest and middle layer; and an outer adventitia layer comprised of connective tissue. The medial layer is comprised mainly of smooth muscle cells which play a prominent role in re-stenosis of previously treated vessels. It is believed that in reaction to the vessel wall trauma associated with balloon angioplasty, the smooth muscle cells within the medial layer proliferate causing a thickening of the overall vessel wall and consequently, a reduction in the luminal diameter of the vessel. This is also known as hyperplasia of the smooth muscle cells.

In another aspect of the invention, smooth muscle cells of the vessel are selectively destroyed without damage to the non-cellular tissue of the vessel. By selectively destroying smooth muscle cells through irreversible electroporation, the proliferation response of the vessel is suppressed. As irreversible electroporation is a non-thermal treatment modality, adjacent structures are not damaged by the electrical field. As an example, the connective non-cellular tissue of the vessel (collagen, elastin and other extra-cellular components) is not impacted by the non-thermal electrical current. Instead, the treated vessel wall is gradually repopulated with endothelial cells that regenerate over a period of time but do proliferate or thicken into a stenotic lesion.

In another aspect of the invention, the electroporation catheter of the current invention may be used to treat native stenotic lesions as well as stenoses or strictures of other bodily organs. Target treatment areas may include claudication of peripheral arteries, stenotic buildup in dialysis fistulas and grafts, carotid artery stenosis and renal artery strictures as well as venous lesions. Also within the scope of this invention are non-vessel lumens including but not limited to biliary tract blockages, bowel obstructions, gastric outflow strictures as well as any other bodily lumen narrowing or occlusion.

Thus in one aspect of the invention, a method of treating stenotic lesions is presented wherein an electrical field ablates vessel wall cells to prevent re-growth of the lesion after angioplasty or other treatment. By suppressing re-proliferation of vessel wall cells, re-stenosis after angioplasty or stenting may be prevented. In addition, the method described herein may be used in lieu of drug-eluting stents which have demonstrated only limited success in preventing stent re-stenosis. In yet another aspect of the invention, the electrical parameters may be set to create an electrical field that temporarily or reversibly electroporate cellular structures. The smooth muscle cells comprising the target lesion will temporarily permiablize, allowing the transport of a drug into the intracellular structure. Drugs may include anti-stenotic agents that may further prevent smooth cell proliferation or cytotoxic drugs, such as a chemotherapy agent if the stricture is caused by a cancerous growth.

Specific Embodiments

There are a range of different catheter device type configurations which can be used in connection with the present invention. Some examples of devices which could be modified to obtain the basic objects of the invention include the balloon catheter device of U.S. Pat. No. 7,150,723 teaching a medical device including guidewire and balloon catheter for curing a coronary artery. Another catheter device which might be modified to utilize the aspects of the invention is the device of U.S. Pat. No. 7,273,487 disclosing a balloon catheter having a multi-layered shaft with variable flexibility. Still another balloon catheter device is taught within U.S. Pat. No. 7,351,214 disclosing a steerable balloon catheter. Yet another device is taught within U.S. Pat. No. 7,481,800 disclosing a triple lumen stone balloon catheter and method. The present invention is not specific to any of these embodiments and other embodiments can be used to provide various catheter configurations which include first and second electrodes connected to a power source which provides to the electrodes a sufficient amount of electrical energy to carry out irreversible electroporation on substantially all of the cells in the vessel target area without subjecting the target area or surrounding area to thermal damage.

Others have endeavored to develop devices and methods for preventing restenosis. The present invention can be used by itself. However, it is also contemplated to utilize the device and methods of the present invention in combination with other methods for reducing restenosis. A possible example includes the device and method disclosed within U.S. Pat. No. 5,947,889 which discloses a balloon catheter to prevent restenosis after angioplasty and process for producing a balloon catheter.

Those skilled in the art will understand that these specific examples provided here are carried out in order to demonstrate the utility of the present invention and that modification of the devices and methodology may be carried out in order to obtain specific preferred embodiments which are intended to be within the scope of the present invention. An example of a specific embodiment is provided below.

Restenosis following coronary angioplasty represents a major clinical problem. Irreversible Electroporation (IRE) is a non-thermal, non-pharmacological cell ablation method. IRE utilizes a sequence of electrical pulses that produce permanent damage to tissue within a few seconds. Examples provided here show that the left carotid arteries of 8 rats underwent in vivo intimal damage using 2 Fogarty angioplasty catheters. The procedure was immediately followed by IRE ablation in 4 rats, while the remaining 4 were used as the control group. The IRE ablation was performed using a sequence of 10 direct current pulses of 3800 V/cm, 100 µs each, at a frequency of 10 pulses per second, applied across the blood vessel between two parallel electrodes. The electrical conductance of the treated tissue was measured during the electroporation to provide real time feedback of the process. Left carotid arteries were excised and fixated after a 28-day follow-up period. Neointimal formation was evaluated histologically. The use of IRE was successful in 3 out of 4 animals in a way that is consistent with the measurements of blood vessel electrical properties. The integrity of the endothelial layer was recovered in the IRE-treated animals, compared with control. Successful IRE reduced neointima to media ratio ($0.57\pm0.4$ vs. $1.88\pm1.0$, $P=0.02$). The present invention shows that the in vivo results of attenuation of neointimal formation using IRE. The invention provides a method which uses IRE to attenuate neointimal formation after angioplasty damage in a mammal such as a human and provides a method of treating coronary artery restenosis after balloon angioplasty.

Balloon Catheter Embodiments

FIG. 1A illustrates a plan view of an embodiment of the electroporation balloon catheter 10 of the current invention.

Catheter 10 is comprised of a hub 13, a flexible catheter shaft 15 extending distally from hub 13 to an expandable member such as a balloon 19 and terminating at catheter distal tip 17. Hub 13 includes a port opening 21 in communication with a shaft lumen (not shown) for the injection and aspiration of fluid to inflate and deflate the balloon 19 during use. Shaft 15 extends from hub 13 distally through the interior of balloon 19 before terminating in distal tip 17. Balloon 19 is coaxially arranged around catheter shaft 15 near the distal end and is shown in an expanded state. Although not shown in FIG. 1A, catheter 10 may also include a side-arm extension on hub 13 with an opening to allow the insertion of a guidewire to facilitate tracking through the vessel. Extending from hub 13 are electrical cable wires 9 which terminate in connectors 11. Connectors 11 are connected to an electrical generator or electrical power source (not shown) to provide an electrical current to a first and second longitudinal electrodes 25 and 27, which are positioned in a longitudinal arrangement around the outer surface of balloon 19.

Figure 1C:
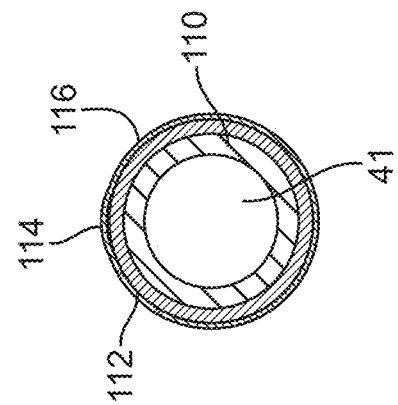
FIG. 1C shows a cross-sectional view of the catheter shaft of FIG. 1A.
Figure 1B:
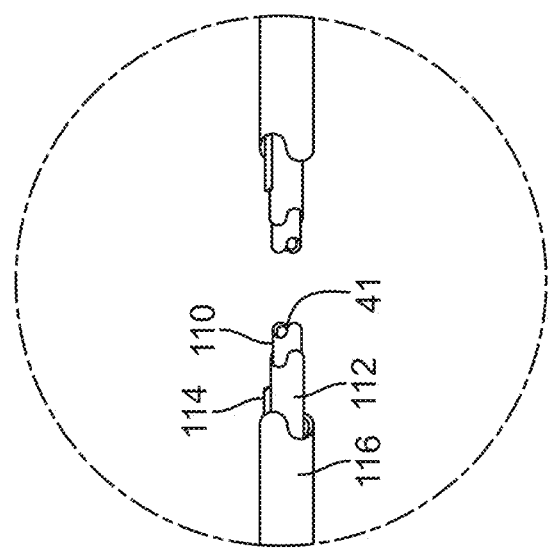
FIG. 1B illustrates an enlarged partial plan view of a catheter of FIG. 1A.

Catheter shaft 15 construction is illustrated in more detail in FIG. 1B, which includes the exploded partial plan view from "A" of FIG. 1A and an enlarged cross-sectional view of the shaft 15 taken along lines B-B of FIG. 1A. As shown in Detail "A" and Section B-B, shaft 15 is comprised of an electrically conductive tubing 110 with a through lumen 41, an insulating layer 112 coaxially surrounding tubing 110 and an outer insulative layer 116 coaxially surrounding the inner insulating layer 112. Wedged between the inner and outer insulating layers 112 and 116, is positioned an electrically conducting wire 114. Inner electrically conductive tubing is preferably comprised of a flexible nitinol shaft or other electrically conductive material to provide a pathway for the electrical current from the electrical generator to the distal end portion of the catheter when in use. It may be dimensioned with appropriate inner diameter and outer diameter. Both the inner and outer insulating layers 112 and 116 are thin layers of appropriate thickness and are made of a non-conductive material such as nylon, polyamide, PET or other plastic material.

The electrically conductive wire 114 is comprised of an electrically conductive material such as nitinol or copper and may be dimensioned at 0.004" thick by 0.015" wide. The inner and outer insulative layers which block electrical current ensure that the electrical current path of the inner electrically conductive tubing 110 remains isolated from the current path of the electrically conductive wire 114. Although not shown in FIG. 1B, in one embodiment, the catheter 10 may include a separate lumen for insertion of a guidewire to assist in advancing the catheter to the target site.

Figure 2:
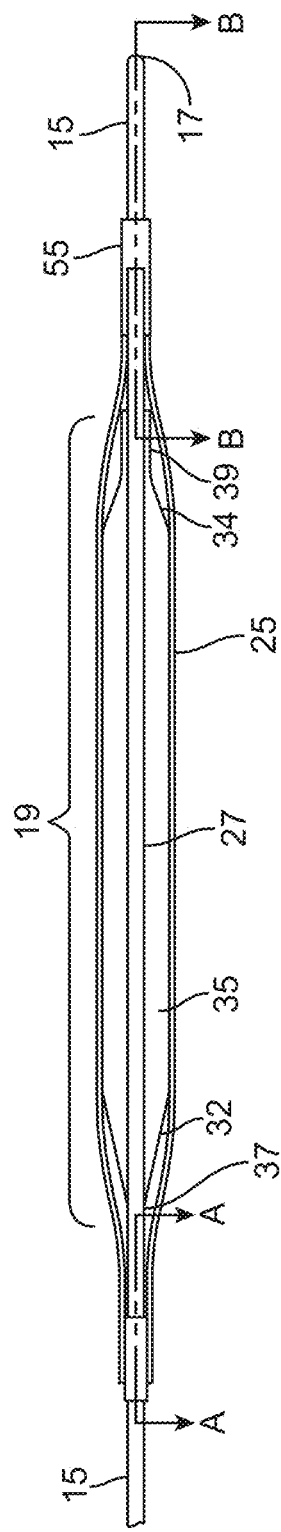
FIG. 2 depicts a plan view of the balloon and electrode assembly of the electroporation balloon catheter of the present invention.

FIG. 2 depicts an enlarged plan view of the distal portion of the preferred embodiment of the electroporation balloon catheter of FIG. 1A in an inflated state. Balloon 19 is coaxially arranged around catheter shaft 15 near the distal end of the shaft. Expanded balloon 19 includes a balloon body 35 portion of constant cross-sectional diameter, proximal 32 and distal 34 cone portions which taper inwardly away from the balloon body 35, and proximal 37 and distal 39 neck portions of reduced diameter relative to the balloon body 35. Neck portions 37 and 39 are bonded to the outer surface of the catheter shaft 15 using adhesive or other bonding methods known in the art. Also illustrated is electrode assembly 26, which is comprised of first and second longitudinal electrodes 25 and 27. The two longitudinal electrodes overlap to form a cage with a series of legs arranged to be in contact with the surface of the balloon when inflated.

Referring to FIGS. 3A and 3B, first and second longitudinal electrodes 25 and 27 are shown prior to assembly with the balloon. The electrodes are comprised of suitable electrically conductive material including but not limited stainless steel, gold, silver and other metals including shape-memory materials such as nitinol. Nitinol is an alloy with super-elastic characteristics which enables it to return to a pre-determined expanded shape upon release from a constrained position.

FIG. 3A which depicts the unassembled first longitudinal electrode 25 which includes a proximal collar 40 with lumen 49 through which is located catheter shaft 15 when assembled. Flexible first and second electrode legs 44 and 42 extend from collar 40 in a distal direction to leg end portions 48 and 46 respectively. The legs 44 and 42 take on the general profile of the expanded balloon shape as can be seen by tapered portions 51, 52, 53 and 54 which correspond with the proximal and distal balloon cone sections 32 and 34. A plurality of electrically insulative elements 105 and 107 covers portions of the first longitudinal electrode 25. The electrically insulating elements 105 and 107 may be of a PET, polyamide or other similar material in the form a tubular structure or heat-shrinkable material. As shown in FIG. 3A, insulative element 105 covers the proximal collar 40 and proximal tapering portions 51 and 52 of electrode legs 44 and 42. The insulating element 105 terminates at a point on the electrode legs 44 and 42 that correspond with the junction of the proximal balloon cone and body (reference FIGS. 2A and 2B). In a similar manner, insulative element 107 covers the distal portions of legs 44 and 42 and extend proximally from distal leg ends 48 and 46, taper portions 53 and 54 to a point on the legs 44 and 42 that correspond with the junction of the distal balloon cone and balloon body. The arrangement of the insulative elements over the legs 44 and 42 create an active electrode portion 45 and 47 through which electrical current will freely pass.

FIG. 3B illustrates the unassembled second longitudinal electrode 27, which is comprised of a distal collar 55 including lumen 65 through which the distal portion of catheter shaft 15 is positioned when assembled. Extending proximally from collar 55 are a first electrode leg 57 and second electrode leg 59 which terminate in proximal leg ends 61 and 63 respectively. Electrode legs 57 and 59 take on the general profile of the expanded balloon shape as can be seen by proximal tapered portions 69 and 70 which correspond with the proximal balloon cone section 32. Distal tapered portions 67 and 68 correspond with the distal balloon cone section 34. Proximal and distal outer insulative layers 101 and 103 cover portions of longitudinal electrode 27. As shown in FIG. 3B, distal insulative layer 103 covers the distal collar 55 and tapered portions 67 and 68. Distal insulative layer 103 terminates at a point on the legs 57 and 59 which correspond with the junction of the distal balloon cone and balloon body (reference FIGS. 2A and 2B). In a similar manner, proximal outer insulative layer 101 covers the proximal portions of legs 57 and 59 and extends from proximal leg ends 61 and 63, tapered portions 69 and 70 to a point on the legs 57 and 59 that correspond with the junction of the proximal balloon cone and balloon body. The straight, un-insulated portion of legs 57 and 59 are the active electrode portions 77 and 79. While the insulated portions of electrode 27 will not conduct electrical current, the active electrode portions 77 and 79 of longitudinal electrode 27 will generate a therapeutic electrical field when electrical energy from the electrical generator is applied to the assembly.

When assembled, first and second longitudinal electrodes 25 and 27 are in an overlapping arrangement relative to each other as shown in FIG. 4A, which illustrates the electrode assembly 26 with second longitudinal electrode 27 rotated 90 degrees clockwise from the view in FIG. 3B. Second longitudinal electrode 27 is positioned in an overlapping relationship with first longitudinal electrode 25 such that collar 55 of second electrode 27 extends distally beyond the leg ends 48 and 46 of first electrode 25. In a similar manner, collar 40 of first electrode 25 extends proximally of leg ends 61 and 63 of second longitudinal electrode 27. When assembled together, the active electrode portions 45, 47, 77 and 79 of both electrodes 25 and 27 are in alignment with each other relative to the longitudinal axis of the electrode assembly 26 and together form an active electrode region 115.

The electrode assembly 26 of FIG. 4A is held together as a single unit at the proximal 40 and distal 55 collars. Specifically, distal portions of legs 44 and 42 of electrode 25 are immovably attached to the outer surface of collar 55 of second longitudinal electrode 27. Conversely, proximal sections of legs 57 and 59 of electrode 27 are immovably attached to the outer surface of collar 40 of first longitudinal electrode 25. Various methods known in the art such as welding, bonding, or application of adhesive may be used to form the attachment between the collars and legs.

FIG. 4B illustrate end views of the electrode assembly 26 taken from line A-A and B-B of FIG. 4A. Referring first to Detail A-A, proximal collar 40 is shown with through lumen 49 and surrounding outer insulative layer 105. Outwardly tapering sections 51 and 52 with insulative layer 105 of first longitudinal electrode 25 are shown extending distally from collar 40 to reach a larger constant diameter of legs 44 and 42. The proximal most ends 61 and 63 of second electrode 27 are shown bonded to the outer surface of collar 40/insulative layer 105 at weld joints 73 and 75 respectively. Outwardly tapering sections 69 and 70 extend horizontally and distally from collar 40 to reach a larger constant diameter of legs 57 and 59 respectively. A partial view of distal collar 55 of second longitudinal electrode 27 with insulative layer 103 is also shown.

Detail B-B of FIG. 4A illustrates an end view of electrode assembly 26 taken along line B-B in FIG. 4A. Distal collar 55 is shown with through lumen 65 and outer insulative layer 103. A partial view of proximal collar 40, which is of a smaller diameter than distal collar 55, is shown within lumen 65. Outwardly tapering sections 67 and 68 of conducting element 27 are shown extending from collar 55 to reach a larger constant diameter of legs 57 and 59. The distal ends 48 and 46 of first longitudinal electrode 25 are shown bonded to the collar 55 of weld joints 62 and 64 respectively. Other attachment methods may be used to create joints 62 and 64, as is known in the art. Outwardly tapering sections 53 and 54 of electrode 25 are shown extending vertically and proximally from collar 55 to reach a larger constant diameter of legs 44 and 42 respectively.

In operation, first and second longitudinal electrodes 25 and 27 each may carry an opposite polarity electrical charge. For example, first electrode 25 may carry a negative electrical charge and second electrode 27 may carry a positive electrical charge. As a result of this arrangement, an electrical field is created between active electrode zones 115 of the first and second electrodes 25 and 27 which are of opposite polarity. For example an electrical current may be created between positively charged leg 57 of second electrode 27 and negatively charged leg 44 of first electrode 25. In the same manner, an electrical current may be created between legs 44 and 59, between legs 59 and 42, and between legs 42 and 57.

As will be explained in more detail below, the resulting electrical field created by the application of electrical energy of opposite polarities to the legs of the first and second creates a substantially 360 degree electrical field zone surrounding the balloon, which when inflated is in contact with the inner wall of the vessel. Consequentially, the entire circumference of the inner wall of the target vessel is subject to a therapeutic electrical field. The electrical field is restricted to the active electrode portions 45, 47, 77, and 79 of the longitudinal electrodes 25 and 27 because these portions are not insulated. As previously mentioned, the un-insulated portions of electrodes 25 and 27 correspond to the constant diameter body portion of the balloon. Those portions of electrodes 25 and 27 that correspond to the proximal and distal balloon cones 32, 34 and necks 37, 39 are insulated and accordingly will not generate and electrical field. Only the vessel wall is treated; any blood present within the vessel lumen is not impacted by the treatment as no electrical field is generated from the insulated portions of the device.

Figure 5A:
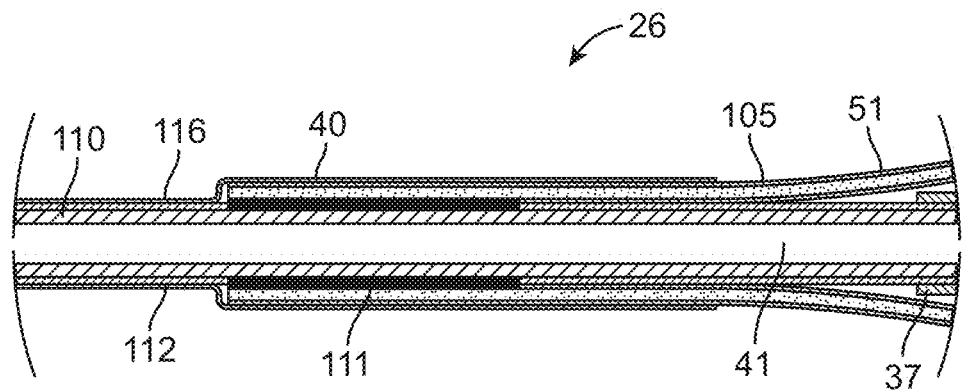
FIG. 5A shows a partial cross-sectional views of the proximal section of the balloon and electrode assembly taken along lines A-A of FIG. 2.
Figure 5B:
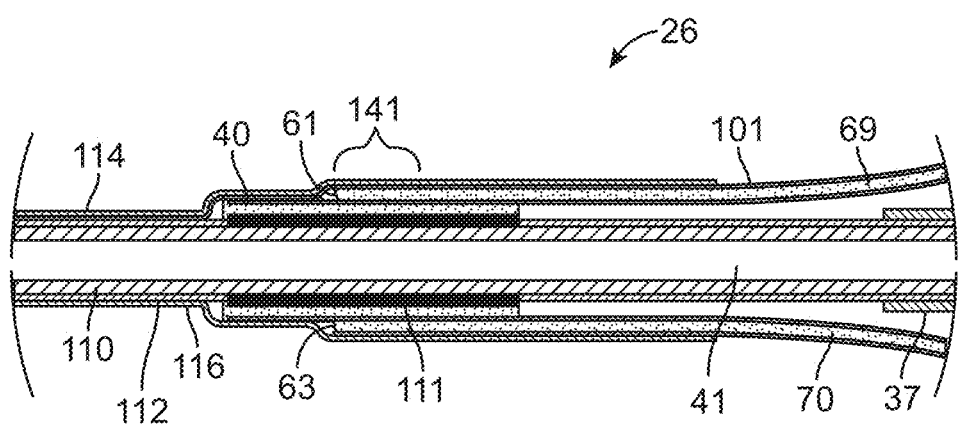
FIG. 5B is a 90° rotated version of FIG. 5A.

FIGS. 5A and 5B illustrate details of the two electrical pathways of electrical current to the active electrode zone 115 (reference FIG. 4A). FIG. 5A illustrates an enlarged cross-sectional partial view of proximal section electrode assembly 26 showing the electrical connection between the wire 114 and the second electrode 27, which in one embodiment may be a positive electrical pathway. Catheter shaft lumen 41 is formed by electrically conductive shaft tubing 110, which includes an outer insulative layer 112, to which collar 40 and proximal balloon neck 37 are attached. Positioned on the surface of insulated shaft 110 is electrically conductive wire 114, which is positioned between insulative layer 112 of the shaft and outer insulative layer 116 to ensure isolation of the positive and negative electrical pathways. At the junction of the shaft 110 and collar 40, electrically conductive wire 114 extends outwardly and distally over collar 40 and over electrode leg 57. The wire is positioned between electrically insulative layer 101 of electrode leg 57 and an outermost insulating layer 116. Layer 116, which extend from hub 13 of catheter 10 (reference FIG. 1A) and over the distal portion of electrode assembly 26, not only ensures that wire 114 is electrically insulated from conductive shaft tubing 110, but also serves to encompasses the various individual component pieces comprising the distal portion of assembly 26.

As shown in FIG. 5A, insulation layer 101 has been removed from the distal portion of leg 57 so as to allow for a direct electrical connection between wire 114 and leg 57 of electrode 27. Wire 114 is attached directly to leg 57 by bonding, welding, soldering or other known means at attachment zone 141. Thus, in one embodiment, the positive polarity electrical current is passed from the generator to the electroporation device 10, electrical energy is transmitted through the shaft by way of the wire 114, to the leg 57 at the un-insulated attachment zone 141 and to the remaining portions of second electrode 27 (reference FIG. 3B). In this manner, the active electrode portions 77 and 79 of legs 57 and 59 (reference FIG. 4A) of longitudinal electrode 27 is energized with positive polarity.

FIG. 5B depicts the proximal section details of the electroporation catheter 10 rotated longitudinally 90 degrees from the FIG. 5A orientation. This cross-sectional view illustrates the second electrical pathway, which in one embodiment is a negative polarity current. Negative electrical current originating from an electrical generator is transmitted through the electrically conductive shaft tubing 110 to collar 40 of electrically conductive element 25. Although shaft 110 includes outer insulative layer 112 for the majority of the shaft length, the layer 112 is removed allowing for direct attachment between shaft 110 and collar 40 at region 111. Region 111 may include a weld bond. The resulting contact region 111 creates an electrical current pathway between the generator and longitudinal electrode 25. Electrical energy will be transmitted through shaft tubing 110 to the collar 40 at contact region 111 and to active electrode regions 45 and 47 of electrode legs 42 and 44. Thus, with this overlapping arrangement of electrodes 25 and 27, electrical energy of opposite polarities is transmitted to the electrically active portion of each pairs of longitudinal legs.

Figure 6A:
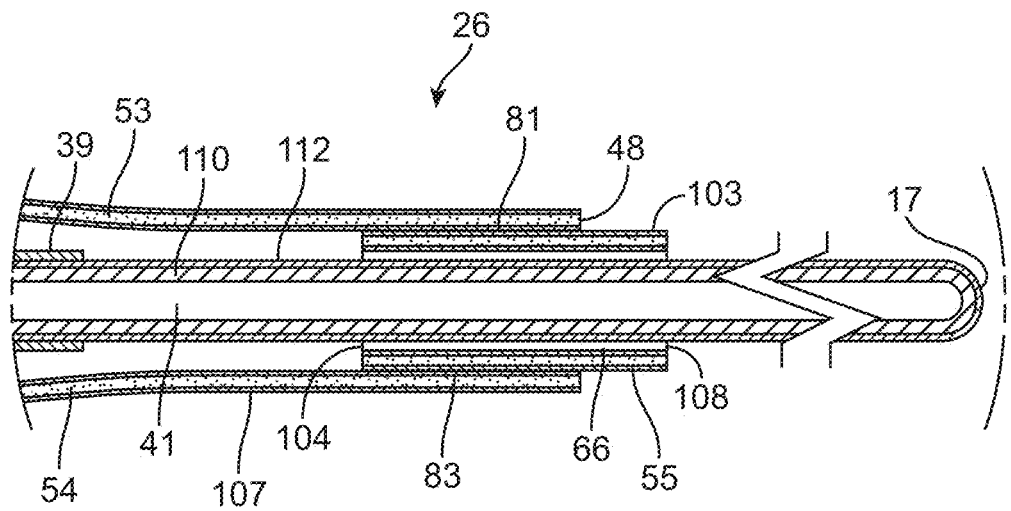
FIG. 6A depicts partial cross-sectional views of the distal section of the balloon and electrode assembly taken along lines B-B of FIG. 2.
Figure 6B:
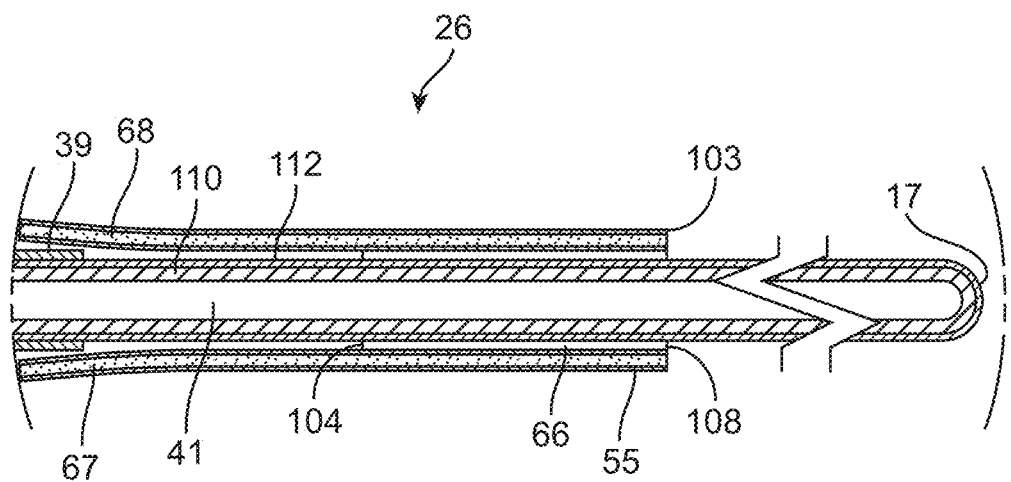
FIG. 6B is a 90° rotated version of FIG. 6A.

The distal portion of electrode assembly 26 is illustrated in two enlarged, cross-sectional partial views of FIG. 6. The second enlarged view is shown at a 90 degree longitudinal rotation from the first view. Electrically conductive shaft 110 is shown with outer insulative layer 112 which extends through the electrode assembly 26 to a distal tip end 17. Coaxially arranged around the insulated shaft 110/112 is the distal neck 39 of balloon 19. Collar 55 of longitudinal electrode 27 also coaxially surrounds shaft 110. Collar 55 is proximate to but not in contact with insulated shaft 110/112. With a catheter shaft of appropriate outer diameter and the collar 40 lumen 65 of appropriate diameter, an annular gap 66 can be made to exist between the two components. Annular gap 66 extends from collar 55 proximal edge 104 to collar distal edge 108. The purpose of gap 66 is to allow electrode assembly 26 to slide freely over shaft 110 as it foreshortens and lengthens during balloon expansion and deflation, as will be explained in more detail with reference to FIG. 8. Also shown in the first view of FIG. 6 are inwardly bowing leg portions 53 and 54 of legs 44 and 42. Insulated legs 44 and 42 are attached to insulated collar 55 at attachment regions 81 and 83 respectively. Adhesive or other known attachment mechanisms may be used to form the connection. Due to the insulative layers 103 of collar 55 and insulative layer 103 of legs 44 and 42, attachment regions 81 and 83 are not electrically conductive and no direct electrical current pathway exists between collar 55 and electrode assembly 25.

FIG. 7 illustrates end views of the balloon 19/electrode assembly 26 taken along lines C-C and D-D of FIG. 1A. Referring first to Section C-C, proximal balloon cone 32 of balloon 19 is shown in an inflated position. Electrode legs 42 extend in a vertical over the surface of balloon 19. Electrically conductive shaft tubing 110 surrounds shaft lumen 41. Collar 40 is in electrical connection with shaft 110 by weld region 111. Collar 40 is coaxially surrounded by electrode assembly insulative layer 101 which electrically isolates collar 40 from wire 114. Outer insulative layer 116 coaxially surrounds the shaft assembly and electrically conductive wire 114. Also shown is an end view of insulative layer 116 as it extends over leg ends 61 and 63.

Detail D-D of FIG. 7 depicts an end view of the catheter assembly taken along lines D-D of FIG. 1A. The distal tip 17 of shaft 19 is positioned within lumen 65 of collar 55 which is also shown as annular gap 66. Electrode legs 57 and 59 extend from collar 55 in a horizontal direction over the surface of balloon 19. Ends 48 and 46 of electrode legs 44 respectively are attached to collar 55 at weld joints 64 and 62.

Figure 8A:
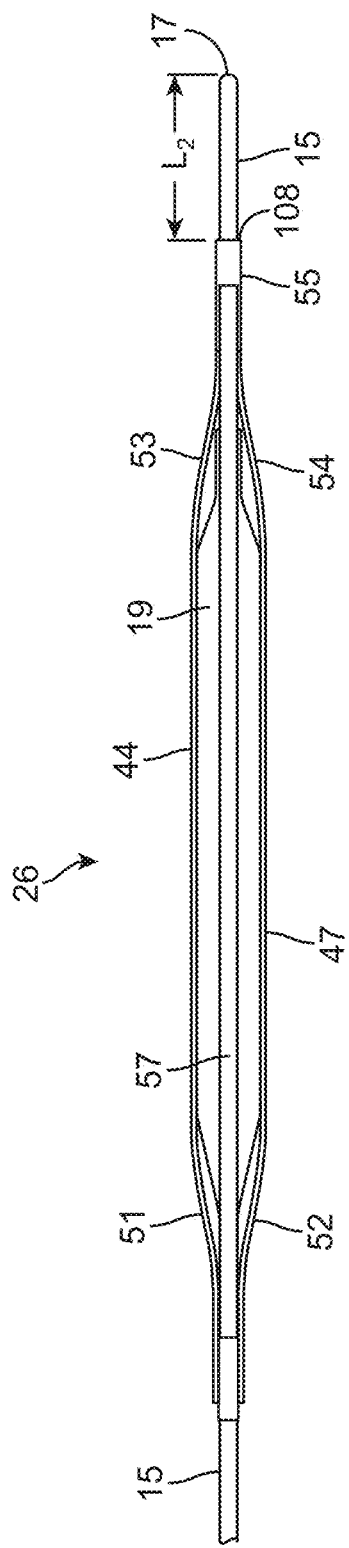
FIG. 8A illustrates a plan view of the combined balloon/electrode assembly in an expanded position.
Figure 8B:
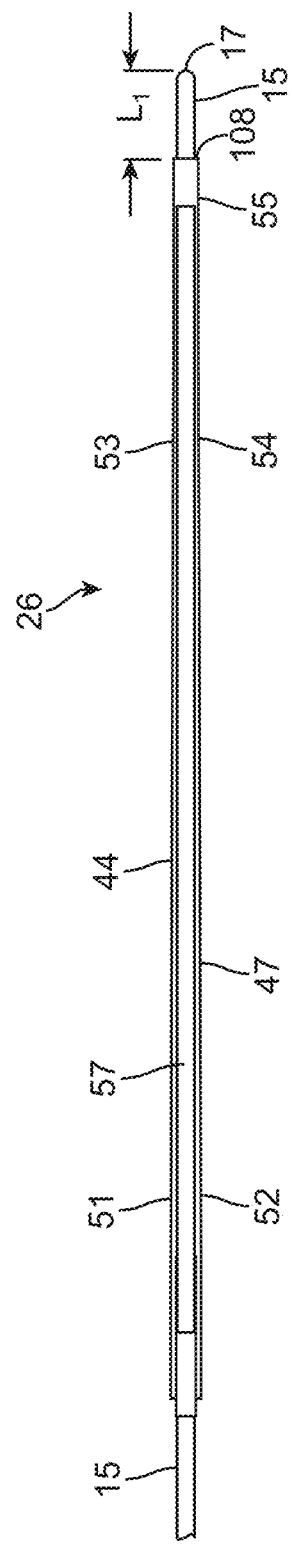
FIG. 8B illustrates a plan view of the combined balloon/electrode assembly shown in a collapsed position.

FIG. 8A-B illustrates the longitudinal movement of electrode assembly 26 relative to the catheter shaft 19 during use. FIG. 8A depicts catheter 10 with balloon 19 inflated. Assembly 26 is positioned in a surrounding relationship over inflated balloon 35. Legs 44 and 47 are shown with proximal taper portions 51 and 52 bowing radially outward and away from shaft 15. Distal taper portions 53 and 54 are also in an expanded state. In one embodiment the electrode assembly 26 is comprised of shape memory material such as nitinol which returns to a pre-determined shape upon release. As such, assembly 26 may retain its expanded profile as shown in 8A even if the balloon is not inflated. When in its natural, unconstrained state, the distal edge 108 of collar 55 is positioned a distance L1 from the catheter distal tip 17.

In a constrained state, as shown in FIG. 8B, electrode assembly 26 is in a collapsed position around shaft 15 and balloon 19. Legs 44, 47, 57 and 59 (not visible) become linear in profile with all tapering portions 51, 52, 53 and 54 flattening out so that they are positioned parallel with the shaft. When the assembly is collapsed, collar 55 slides in a distal direction. Movement of the electrode assembly 26 relative to the shaft 19 and balloon 25 occurs because the distal portion assembly 26 is not attached to shaft 15 at collar 55. When electrode assembly 26 is completely collapsed, the leading edge 108 of collar 55 is positioned a distance L2 away from catheter distal tip 17. Total distal movement of the assembly collar 55 is for a length of L1-L2. More specifically, catheter 10 is typically inserted into a target vessel through a sheath or other introducer device.

Figure 9:
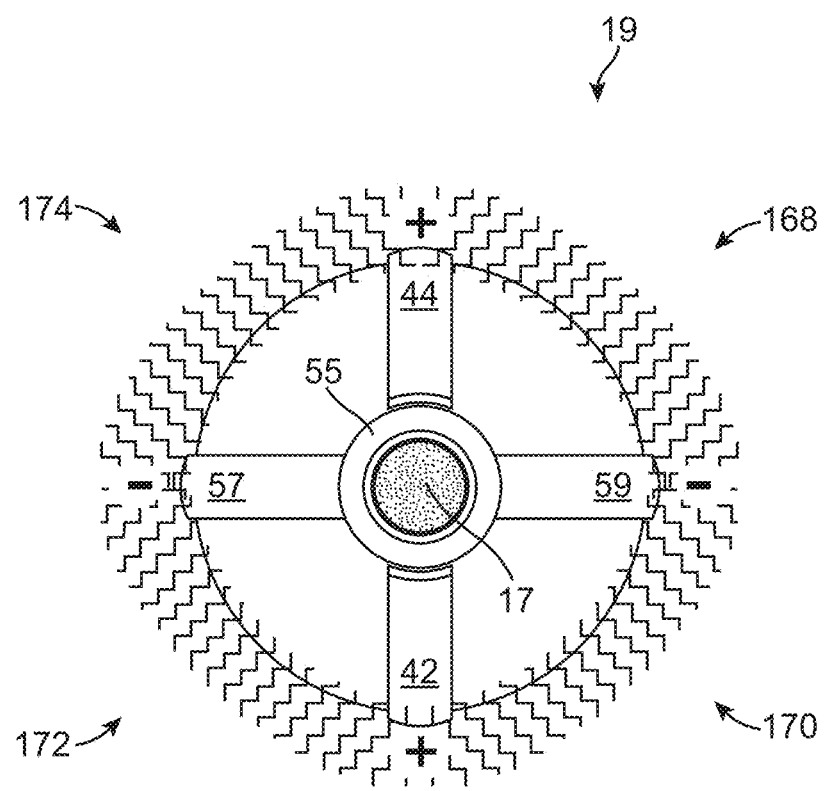
FIG. 9 shows an end view of the balloon electrode assembly taken along lines D-D of FIG. 1 illustrating the electrical current generated between the electrodes.

FIG. 9 illustrates the electrical current flow pattern from an end view of the electroporation catheter device 10. Electrical energy will be transmitted from an electrical generator through shaft tubing 110 to electrode legs 42 and 44 of electrode assembly 25 as previously described. In one embodiment, this electrical pathway is of a positive polarity as indicated by the "+" signs in FIG. 9. Electrical energy of a negative polarity may be transmitted through wire 114 to longitudinal electrode assembly 27 through wire 114 to leg 59 connection 111. In one embodiment, this second electrical pathway is of a negative polarity as indicated by the "−" signs in FIG. 9. The electrodes can be electrically energized one pair at a time and selectively switched to cover all four pairs. In the embodiment shown, all electrodes are simultaneously energized, causing electrical current to flow from positive polarity legs to negative polarity legs. As an example, electrical current will flow from leg 44 with a positive polarity to leg 59 with a negative polarity, creating an electrical field zone 168. Electrical current from leg 59 will also flow to negative polarity leg 57, creating an electrical field zone 174. In a similar manner, positive polarity leg 42 will transmit electrical current to both negative polarity legs 57 and 59, creating electrical fields 172 and 170. Although not shown in FIG. 9, the flow of electrical current will be restricted to the un-insulated portions of the electrode legs, which correspond with maximum diameter of the inflated balloon 19. The resulting combined electrical fields created by the application of electrical energy of opposite polarities to the electrode legs 44, 59, 42 and 57 create a substantially 360 degree electrical field zone surrounding the balloon body 35. When the catheter is in position in a target vessel, this combined electrical field zone extends radially outward and into the inner wall of the vessel. In this manner, the entire circumference of the inner wall of the target vessel is subject to a therapeutic electrical field.

Figure 10:
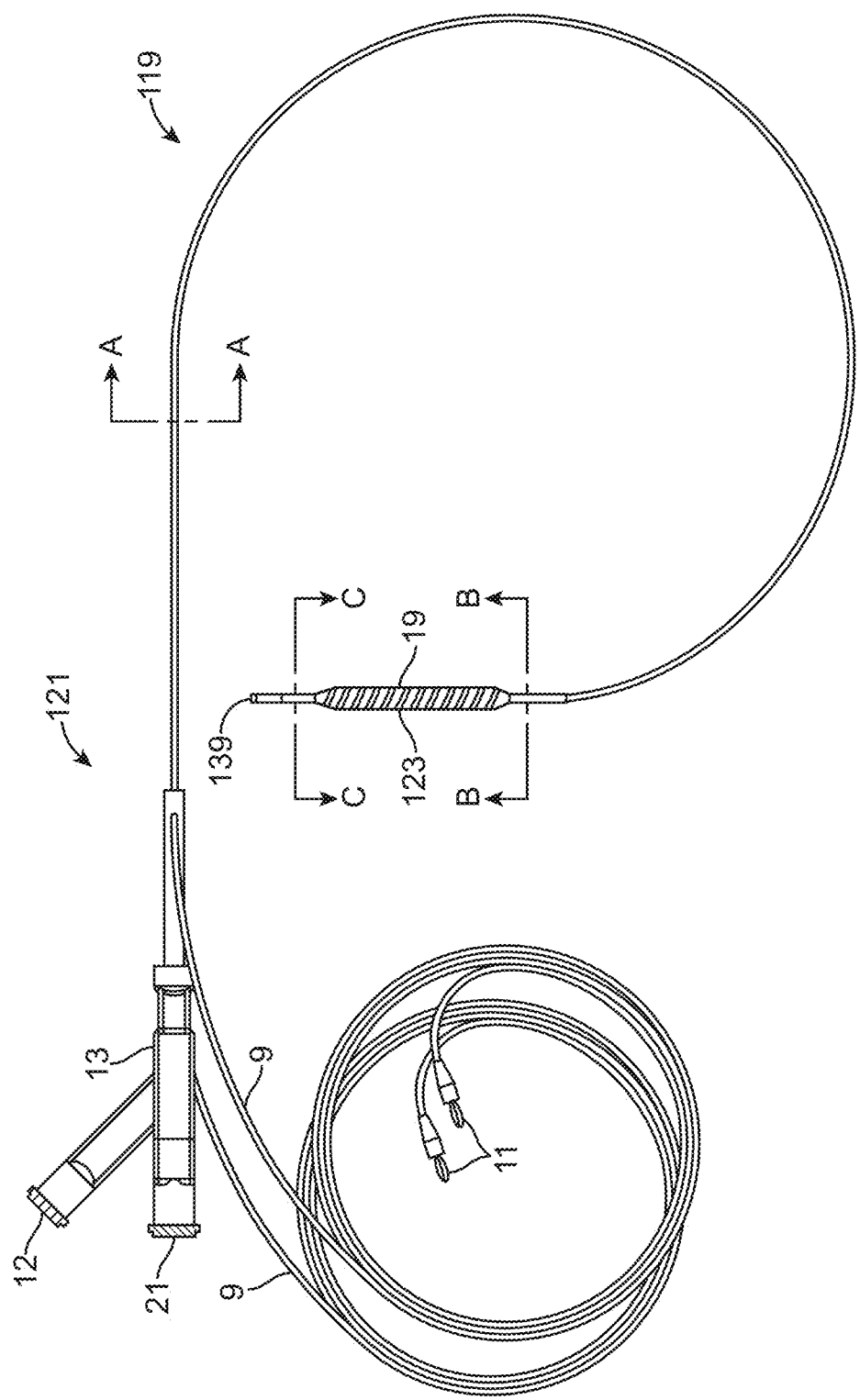
FIG. 10 is a plan view of another embodiment of an electroporation balloon catheter of the present invention with a balloon and electrode assembly at the distal portion of the catheter.

An alternative embodiment of the electroporation balloon catheter of the present invention with a balloon and electrode assembly is shown in a plan view in FIG. 10. Catheter 121 is comprised of a hub 13, a catheter shaft 119 extending distally to a balloon 19 and terminating at a catheter open distal end 139, which is sized to pass a guidewire. Balloon 19 is coaxially arranged around catheter shaft 119 near the distal end and is shown in an expanded state. Hub 3 may include port opening 13 and side-arm extension opening 12 to allow the insertion of a guidewire and injection of fluid to inflate the balloon 19. Extending from hub 3 are electrical cable wires 9 which terminate in connectors 11. Connectors 11 are connected to an electrical generator (not shown) to provide an electrical current to the spiral electrode assembly 123 which is coaxially arrangement over balloon 19.

Figure 11:
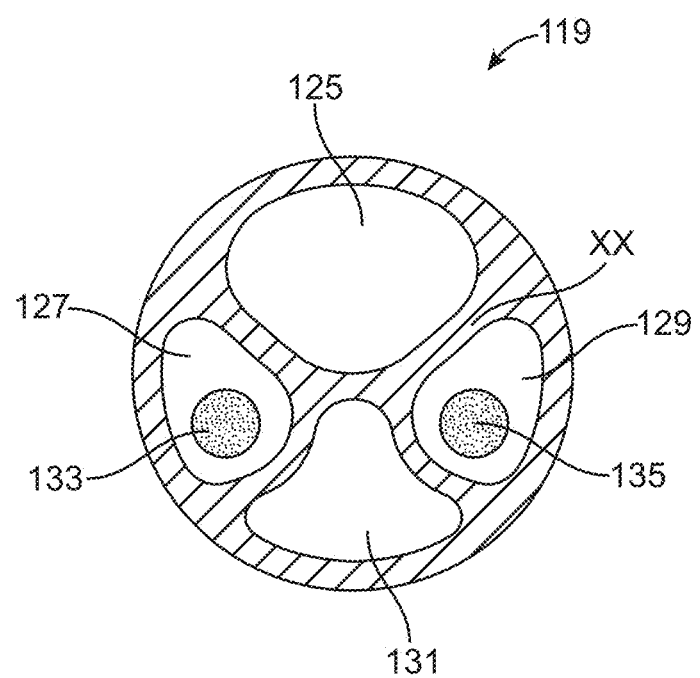
FIG. 11 illustrates an enlarged cross-sectional view of the catheter shaft of FIG. 10 taken along lines A-A.

FIG. 11 represents a cross-sectional view of the catheter shaft 119 taken along lines A-A of FIG. 10. Shaft 119, which in one embodiment has a sufficient outer diameter so that it may include four lumens. Guidewire lumen 125 may be approximately 0.039" in diameter and in communication with side arm extension opening 1 to accept a standard guidewire which is used for tracking device 121 to the target location within a vessel. Inflation/deflation lumen 131 is in communication with hub opening 21 for injection and withdrawal of fluid to and from the balloon 35 interior. First and second electrode wire lumens 127 and 129 are configured to contain electrode wires 133 and 135 respectively. Wires 133 and 135 are electrically insulated from each other by inner shaft septum 137, which is comprised of a plastic or other non-conductive material.

Figure 12:
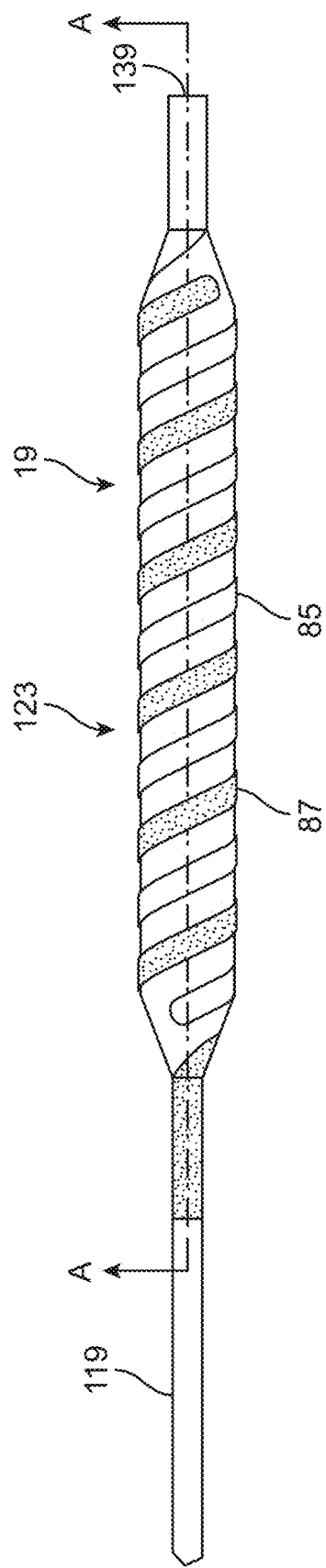
FIG. 12 is a plan view of the balloon and electrode assembly of the electroporation balloon catheter of FIG. 10.

FIG. 12 illustrates an enlarged plan view of the distal end section of the electroporation balloon catheter 121 which is shown inflated. Catheter shaft 119 extends into and through balloon 35, terminating at open distal tip 139. Helically surrounding the balloon surface is spiral electrode assembly 123, which is comprised of a first and second spiral electrode 85 and 87. In one embodiment, first spiral electrode element 85 is of a positive polarity and second electrode 87 is of a negative polarity. Spiral electrode 85 is connected to first electrode wire 133 and spiral electrode 87 is connected to second electrode wire 135.

Figure 13A:
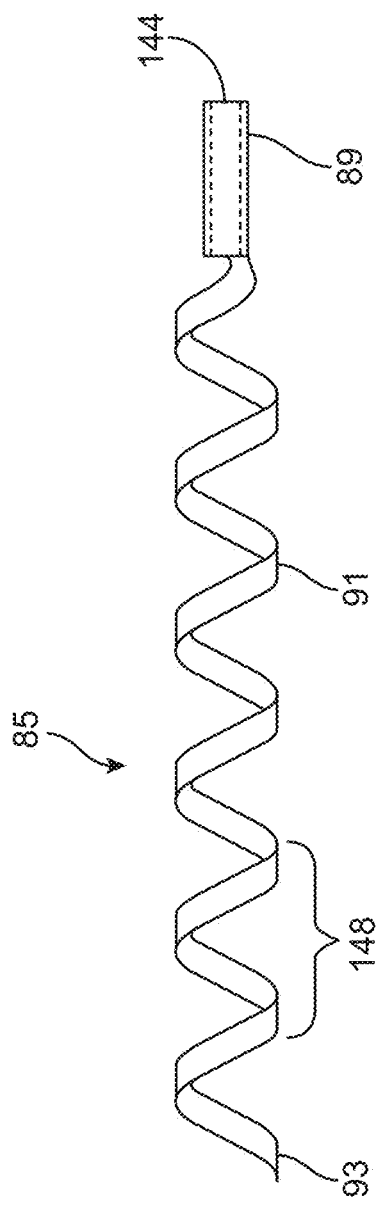
FIG. 13A is a plan view of a first spiral electrode of the electrode assembly of FIG. 10.
Figure 13B:
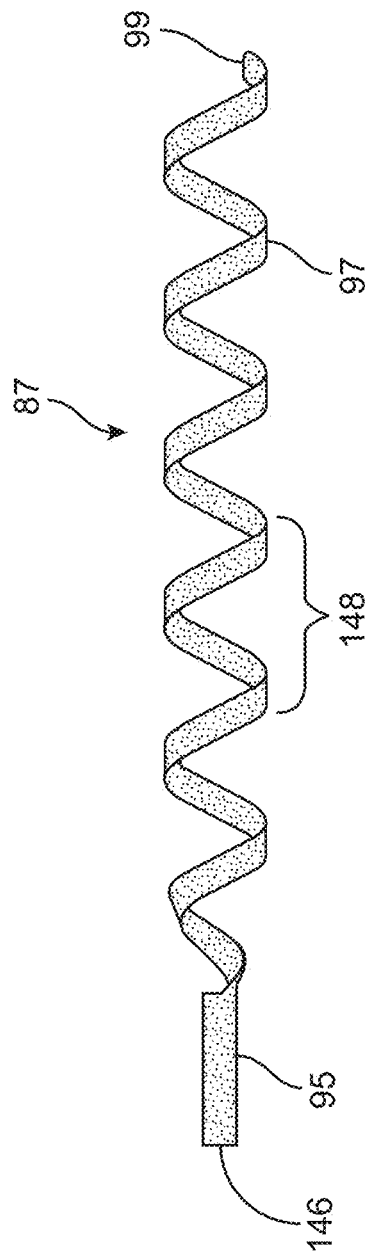
FIG. 13B is a plan view of the second spiral electrode of the electrode assembly of FIG. 10.
Figure 14:
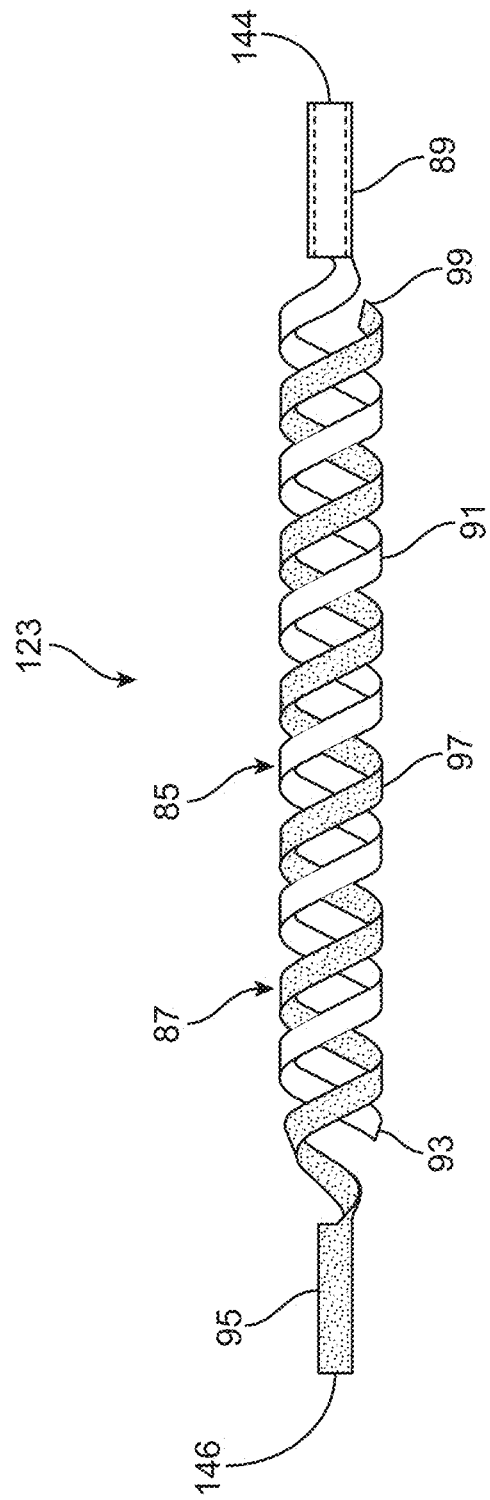
FIG. 14 illustrates a plan view of a spiral electrode assembly comprising the first and second spiral electrodes.

Details of the spiral electrodes are shown in FIG. 13. First spiral electrode 85, shown in FIG. 13A, is comprised of a distal collar 89 containing a lumen 144, a spiral shaped body 91 of an expanded diameter relative to the collar 89 and a proximal tail 93. A second spiral electrode 87 is shown in FIG. 13B. Second spiral electrode 87 is comprised of a proximal collar 95 with through lumen 146, a spiral shaped body 97 of an expanded diameter relative to collar 95, and a distal tail 99. The spiral shaped bodies 91 and 97 are formed of a series of helical turns 148. The two spiral electrodes 85 and 87 may be assembled together in an overlapping relationship on the same longitudinal axis to form a double helix was shown in FIG. 13C. The plurality of helical turns 148 of the first spiral electrode 85 are positioned adjacent to corresponding helical turns 148 of the second spiral electrode 87.

Electrode 85 and 87 may be comprised of any conductive material known in the art. For example, the electrodes may be formed of a nitinol tube which has been laser cut and memory set to the desired spiral profile. Alternatively, electrodes 85 and 87 may be comprised of a conductive ink which is applied in the desired pattern to the exterior balloon surface. As an example, the conductive ink may be comprised of an adhesive binder material loaded with silver particles. Other conductive materials such as gold or steel may also be used. In one embodiment, the conductive ink may be applied in the desired pattern to the balloon surface using a pen-like applicator and a rotating lathe type fixture. The application of conductive ink may be between 0.001" and 0.002" in thickness.

Figure 15A:
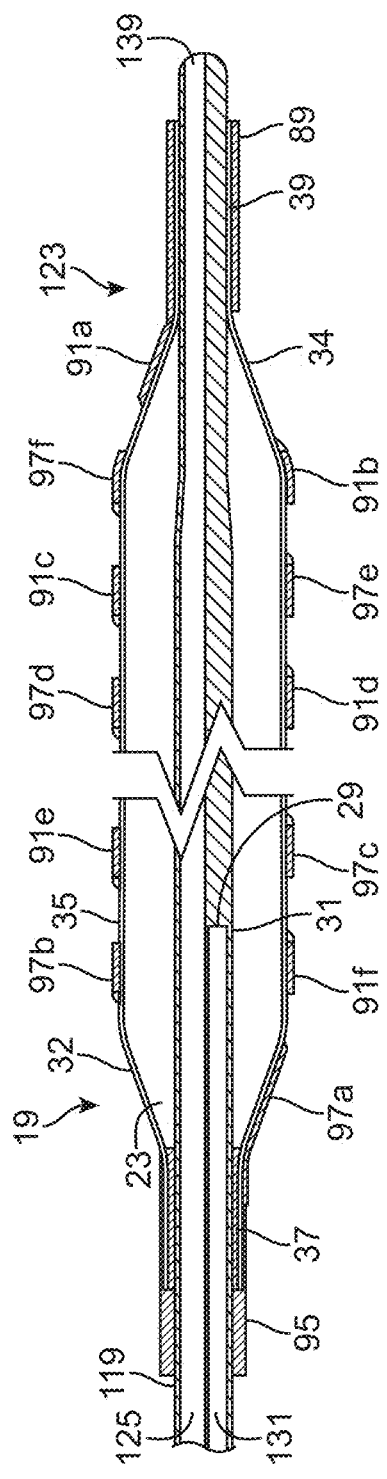
FIG. 15A is a partial longitudinal cross-sectional view of the distal portion of the electroporation catheter taken along lines A-A of FIG. 12 illustrating the electrodes, shaft and balloon.

FIG. 15A illustrates an enlarged cross-sectional view of the spiral electrode assembly 123 positioned on the outer surface of the balloon. The cross-sectional view is taken along lines A-A of FIG. 12. Shaft 119 is includes a guidewire lumen 125 and an inflation lumen 131. The guidewire lumen 125 extends from catheter hub 3 through shaft 119 exiting at open distal end 139. The inflation lumen 131 also extends from catheter hub 13 (reference FIG. 10) but terminates within balloon interior 23 at inflation lumen dead end 29. In operation, a fluid or other inflation medium is injected into hub 13 through hub opening 21, directed distally within inflation lumen 131 and into the balloon interior 23 through inflation lumen side port 31. This fluid path is also used for withdrawing fluid to deflate the balloon prior to withdrawal of the device from the target vessel.

First spiral electrode 85 is positioned over balloon 19 with distal electrode collar 89 coaxially surrounding distal balloon neck 39. In one embodiment, first spiral electrode 85 is of a positive polarity. Extending proximally from electrode collar 89, electrode section 91*a* partially surrounds balloon cone 34 and comprises the beginning of the first helical turn. The spiral electrode 85 pattern continues proximally along the surface of balloon body 35, as illustrated by electrode cross-sections 91*b*, 91*c*, 91*d*, 91*e* and 91*f*. The proximal tail 93 of the first electrode spiral is not visible, but is positioned adjacent to proximal balloon cone 32. A second or negative spiral electrode 87 includes a proximal collar 95 that coaxially surrounds balloon proximal neck 37. Extending distally from collar 95, electrode section 97*a* partially surrounds proximal balloon cone 32 and comprises the beginning of the spiral pattern. The negative electrode spiral pattern continues proximally along the surface of the balloon body 35, as illustrated by electrode cross-sections 97*b*, 97*c*, 97*d*, 97*e* and 97*f*. The distal tail 99 of negative spiral electrode is not visible, but is positioned adjacent to the balloon cone 34.

The resulting surface pattern of the combined spiral electrodes 85 and 87 is a double helix configuration with alternating polarity electrodes positioned along the balloon surface. When electrical current of opposite polarity is applied to electrodes 85 and 87, an electrical field is generated between the positive spiral electrode 85 and the negative spiral electrode. With the electrical current flowing from positive to negative, an electrical field is created between each set of helical turns. As an example, electrical current will flow from 91*a* to 97*f*, from 91*b* to 97*e* and from 91*c* to 97*d*. The effect of this electrical field pattern is that the majority of the balloon surface is within the active electrical field. This is advantageous in that since the electrical field encompasses substantially the entire balloon surface, the resulting ablation zone will uniformly encompass the vessel wall area corresponding to the balloon surface.

Figure 15B:
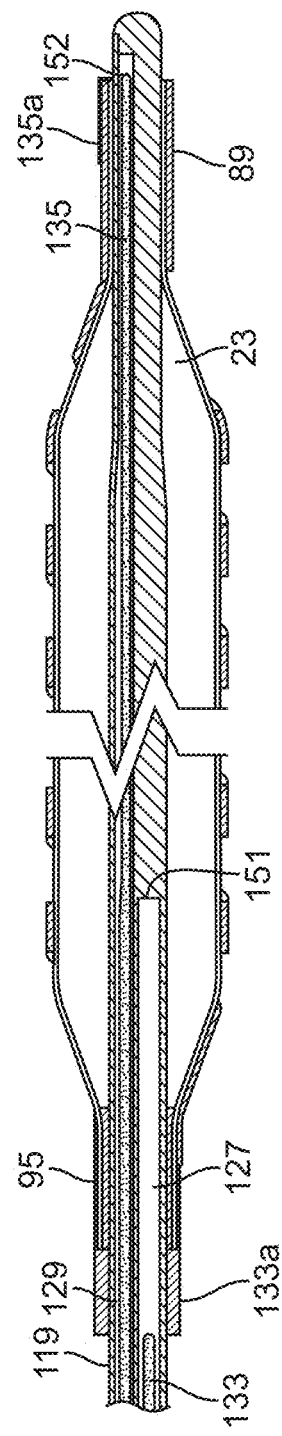
FIG. 15B is a partial longitudinal cross-sectional view of the distal portion of the electroporation catheter taken along lines A-A of FIG. 12 after 90 degree rotation from FIG. 15A.
Figure 16:
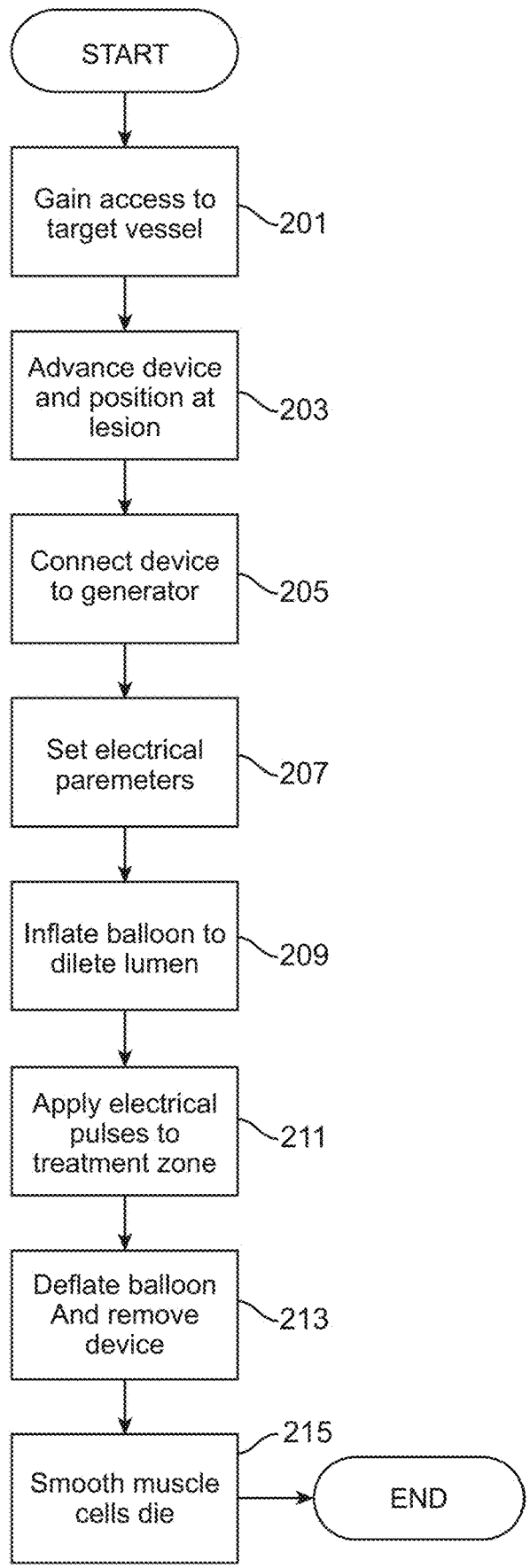
FIG. 16 is a flowchart representing the steps of one method of the invention.

FIG. 15B illustrates an enlarged cross-sectional view of the spiral electrode assembly 123 positioned on the outer surface of the balloon 35 and represent a 90 degree rotation of the cross-sectional view of FIG. 15A. This shows the electrically conductive wires 133 and 135 which are not visible in the FIG. 15A cross-section. Electrically conductive wires 133 and 135 originate within cable connectors 11 and extend distally within cable lines 9 and enter shaft lumens 127 and 129 through hub 3. Both wires are comprised of an electrically conductive material such as silver, gold, copper or other metal. In one embodiment, wires 133 and 135 have a flat profile with dimensions of approximately 0.004" thick and 0.015" wide. In another embodiment the wires may be circular in cross-sectional diameter. An insulative outer layer may surrounds the bare wire. The insulative layer may be of a plastic material such as nylon.

Each wire has a dedicated lumen within shaft 119, as shown in FIG. 15B. Electrically conductive wire 133 is coaxially arranged within lumen 127 and. Electrically conductive wire 135 is coaxially arranged with lumen 129. The separate, dedicated wire lumens 127 and 129 provide additional assurance that the electrically conductive wire 133 and 135 which are of opposite polarity when charged, are electrically isolated from each other for the entire length of the catheter shaft. Both lumens 127 and 129 terminate within shaft 119 body forming closed ended lumens so that the electrically conductive wire elements 53 and 55 and lumens 65 and 66 are not exposed to air or bodily fluids which may compromise the electrical field.

Electrically conductive wires 127 and 129 are in connection with spiral electrodes 85 and 87 at electrode collars 95 and 89 respectively. Electrode wire 133 exits electrode wire lumen 127 at side port exit 150 just proximal to electrode collar 95. Upon exit, electrically conductive wire 127 is attached to the outer surface of collar 95, whereby completing the electrical pathway between the electrical generator and the spiral electrode 123. Wire 133 is attached to the spiral electrode collar 95 using either a conductive epoxy or other attachment method known in the art. In a similar manner electrode wire 135 exits wire lumen 129 at a side port exit 152 just distal to the electrode collar 89. Upon exit, electrically conductive wire 129 is attached to the outer surface of collar 89, whereby establishing the electrical pathway to the spiral electrode 85. In an alternative embodiment, electrically conductive wire 135 may exit wire lumen 129 within the balloon interior 45. In this embodiment, the insulated wire 135 is sandwiched between the distal balloon neck 39 and the outer surface of catheter shaft 119, exiting from the distal end of balloon neck 39 to make contact with electrically conductive collar 89.

Other embodiments of the electroporation catheter of the current invention are shown in FIG. 18A-D. FIG. 18A illustrates an alternative embodiment of the balloon electrode assembly 401 comprising two electrodes 403 and 405 of opposite polarity. Proximal electrode 403 covers the proximal neck, cone and a portion of the body of the balloon 407 and in one embodiment is comprised of a conductive ink coating. Other metallic materials may be used to manufacture the electrodes. Distal electrode 405 covers the distal neck, cone and a portion of the balloon 407 body. The exposed balloon body portion 409 represents the active electrode zone. In one embodiment, the electrode material is selected so as to be ultrasonically or fluoroscopically visible allowing the user to position the active electrode zone 409 within the lesion based on the location of the proximal electrode leading edge 411 and the distal electrode tailing edge 413. In a separate embodiment, shown in FIG. 18B, balloon electrode assembly 421 may include two or more electrode rings 423 and 425 of opposite polarity. Rings 423 and 425 may be attached to the outer or inner surface of balloon 427, or may be embedded within the balloon wall. This embodiment, with the smaller active electrode zone 429, may be advantageous when treating smaller length lesions. The embodiments of both FIG. 18A and FIG. 18B are also advantageous in that these designs are easy to manufacture.

In yet another embodiment of the invention the balloon electrode assembly 431 may be comprised of a mesh or woven layer which includes electrodes as shown in FIG. 18C. Balloon electrode assembly includes helically wound strands 433, 435 and 429 covering the surface of balloon 437. Electrode strands 433 and 435 circumferentially surround balloon 437 and are positioned adjacent to and parallel to each other at an angle of approximately 65 degrees relative to the longitudinal axis of the balloon. Strands 433 and 435 may be of a conductive material such as metallic wire. Strand 433 may be of a positive polarity and strand 435 may be negative. Strand 439 is positioned at an opposite angle to strands 433 and 435 and runs circumferentially in a helical pattern around the balloon surface. Stand 439 may be comprised of a non-conductive material including high strength polyester, nylon or other material so as to increase the overall strength of the balloon. In operation, electrical current will flow from the positively strand 433 to adjacent negatively charged strand 435 creating a tubular ablation zone extending radially outward from the balloon body.

FIG. 18D illustrates an embodiment of an electroporation balloon catheter 441 in which a series of opposite polarity prongs 447 and 449 are present in an alternating pattern across the balloon body 451. Electrode 443 is comprised of a plurality of distally extending prongs 447 which may be of a positive polarity. Interspaced between each positive polarity prong 447 are negatively charged proximally extending prongs 449 of electrode 445. The alternating positive and negative polarity electrode prongs create a ablation zone extending radially outward from the balloon body.

The method of using the electroporation balloon catheter of the current invention to prevent re-stenosis of a vessel will now be described with reference to FIGS. 16 and 17A-E. To begin the procedure, access is gained to the vessel using techniques known in the art such as the Seldinger needle/guidewire access technique as shown in step 201 of FIG. 16. The electroporation balloon catheter is inserted into the vessel and advanced to the target lesion (203). In the various embodiments of the catheter previously described, the catheter may be inserted directly through an introducer sheath or may be inserted and advanced over a guidewire to the target vessel lesion. For non-vascular lumens, a direct percutaneous stick or cut down procedure maybe used to access the target area such as a biliary duct.

Figure 17A:
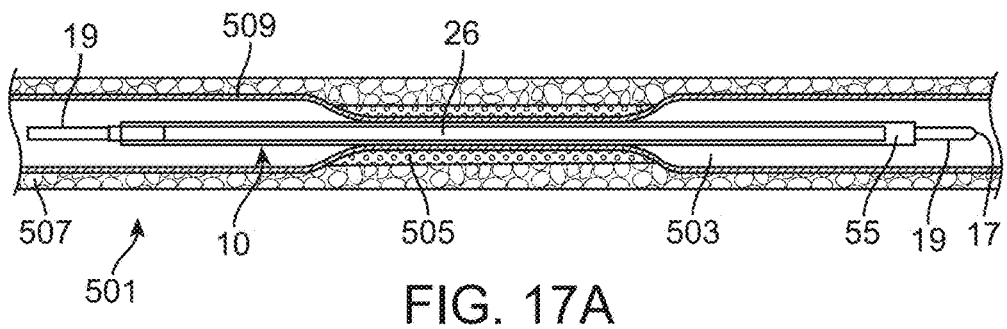
FIG. 17A depicts a step in the method of treatment of restenosis within a vessel.

FIG. 17A illustrates electrode catheter 10 of FIG. 1A in position within the lumen 503 of a vessel 501 to be treated prior to angioplasty. Vessel 501 comprises vessel wall 507 and endothelial inner layer 509. Also shown is the stenotic region 505, which extends into the vessel lumen narrowing the luminal diameter in this area. Electrode balloon catheter device 10 in shown in an unexpanded state within the vessel 507 lumen 503 with the electrode assembly 26 positioned adjacent to the stenotic region 505. Although the longitudinal electrode assembly embodiment 10 of FIG. 1 is shown, any of the described catheter embodiments may used with this method.

Once correctly positioned within the anatomical lumen, electrical connectors 11 of the catheter 10 are connected to an electrical generator (205). This completes an electrical circuit between the electrodes and the generator. This step may be performed at any time prior to applying the electrical pulses to the device. Treatment protocol parameters such as pulse width, number of pulses and voltage are set using the generator interface (207). Typical ranges include but are not limited to a voltage level of between 100-3000 volts, a pulse duration of between 20-100 μsec, and between 10 and 500 total pulses. By varying parameters of voltage, number of electrical pulse and pulse duration, the electrical field will either produce irreversible or reversible electroporation of the smooth muscle cells comprising the inner vessel wall or endothelium 509. In one embodiment of the invention, ten electrical pulses of 3500 V/cm at a frequency of 10 Hz may be used. In another embodiment, 90 electrical pulses of 1750 V/cm at a frequency of 1 Hz may be used. These ranges ensure that damage caused by Joule heating is avoided.

In another aspect of the invention, conductance of the electrical current may be measured during the procedure to monitoring clinical endpoints. As an example, a successful treatment may be identified by changes in conductance during the applied pulses and an overall decrease in conductance. Measuring conductance will make it possible to calibrate the current, voltage, and pulse duration parameters to avoid thermal damage and obtain IRE. The conductance changes when the cells are porated.

Figure 17B:
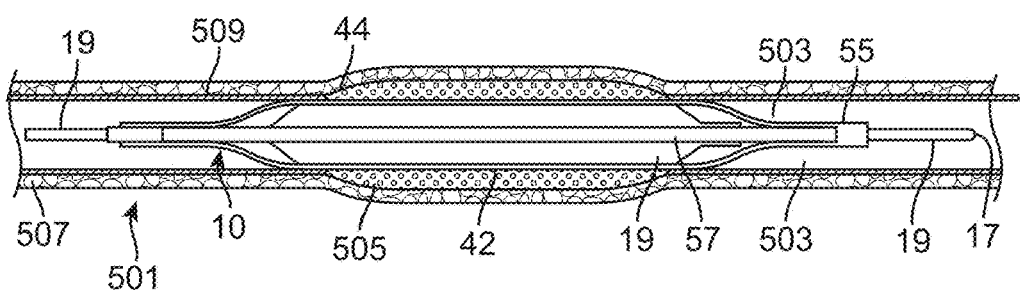
FIG. 17B depicts a step in the method of treatment of restenosis within a vessel.

Referring to FIG. 17B, the balloon 19 is then inflated to dilate the vessel lumen 503 and restore the vessel patency (209). As balloon 19 is inflated, the electrode assembly 26 surrounding the balloon is moved into contact with the stenotic region 505 of vessel wall 507 as shown in FIG. 17B. The stenotic lesion 505 is pushed radially outward by the force of the balloon enlarging the vessel lumen 501. The active electrode region of the electrode assembly 26 is aligned and in contact with the area of the vessel wall 507 that was forced outwardly. Specifically, electrode collar 55 slides proximally along the distal portion of the catheter shaft 19 as the balloon 19 expands, which causes electrode legs 44, 47, 42 and 59 (not shown) to move radially outward relative to the longitudinal axis of the shaft 19. The exposed, un-insulated portions of the plurality of electrode legs come into contact with the endothelial layer 509 of stenotic lesion 505.

Once the lumen has been sufficiently enlarged by angioplasty, electrical pulses of a predetermined pulse width and voltage are applied across the electrodes. Pulses are applied while the balloon remains inflated (211). This provides not only contact between the electrodes and vessel wall, but also ensures that blood is not present in the electrical field. The conductivity of blood is known to be higher than the vessel wall. Accordingly, the treatment may be compromised if a significant amount of blood was present in the target area of the vessel since the electrical current would be directed to the bloodstream rather than the vessel wall.

Figure 17C:
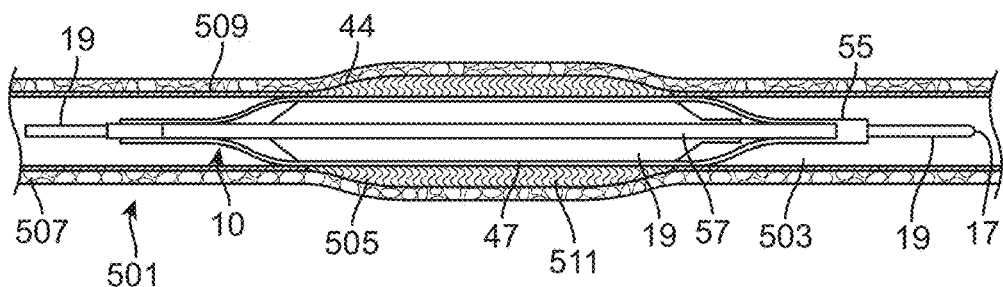
FIG. 17C depicts a step in the method of treatment of restenosis within a vessel.

Based on the electrical parameters chosen as part of the treatment protocol, an electrical field gradient is generated between opposite polarity electrodes of sufficient strength to non-thermally electroporate the smooth muscle cells in the target vessel wall 501. The generated electrical field is represented in FIG. 17C by 505 lines which extend from the expanded balloon 19 through the endothelial layer 509 into the stenotic region 505 of the vessel wall 507 forming a tubular shaped ablation zone corresponding to the interior vessel wall segment being treated. When electrical pulses are administered within the irreversible parameter ranges, permanent pore formation occurs in the cellular membrane, resulting ablation of the smooth muscle cells 509 of the vessel wall. This is the area that is most susceptible to endothelial proliferation due to vessel wall trauma caused by the balloon.

If the electrical generator treatment parameters are set to deliver electrical pulses within the reversible range therapeutic agents may be injected through the catheter lumen to the target lesion site. The agent will be transported to the smooth muscle cell interior through the transient cellular membrane openings. The membrane openings will then close retaining the therapeutic agent within the cell interior. Anti-restenosis drugs such as Paclitaxel and Vasculast as well as other agents known in the field may be introduced into the cell.

Figure 17D:
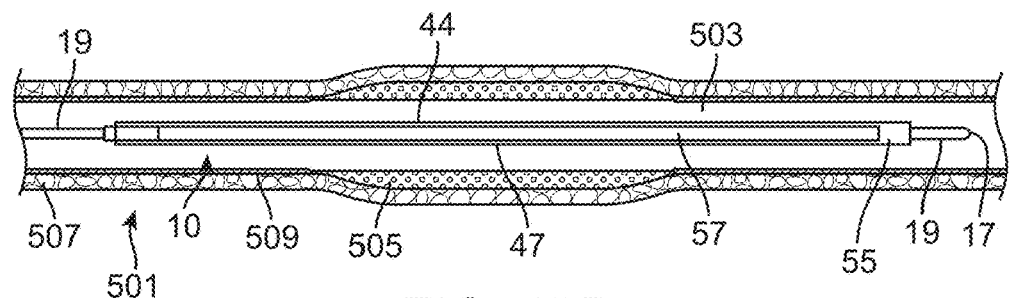
FIG. 17D depicts a step in the method of treatment of restenosis within a vessel.
Figure 17E:
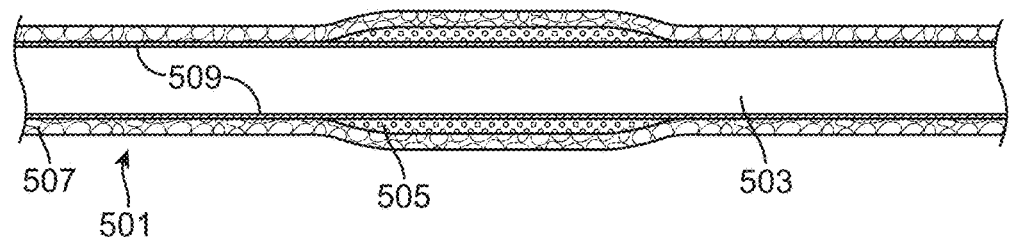
FIG. 17E depicts a step in the method of treatment of restenosis within a vessel.
Figure 19A:
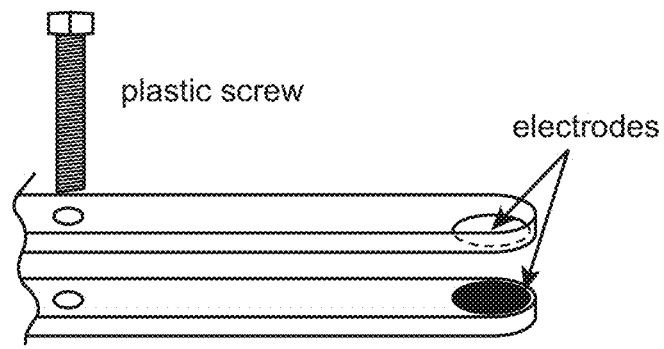
FIG. 19A which is a schematic drawing of the device used in Example 1.
Figure 19B:
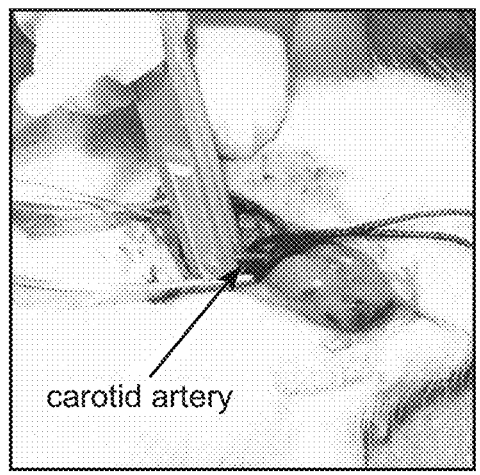
FIG. 19B which is a photograph of a custom made electrode clamp employed to induce irreversible electroporation of the carotid artery.
Figure 20:
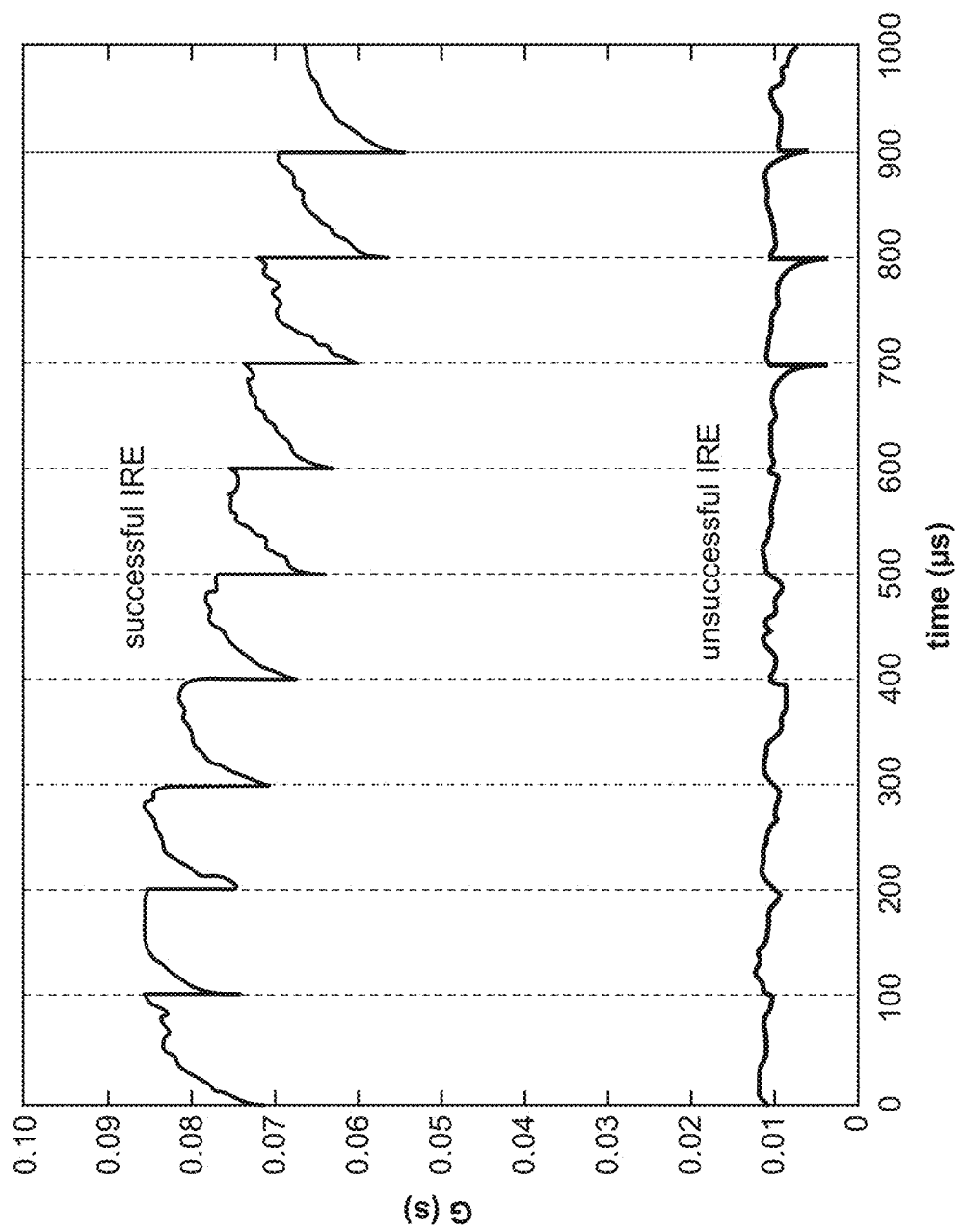
FIG. 20 shows a graph of examples of conductance of the arterial wall during repetitive direct current pulses of the device used in Example 1. Conductance is measured only during the 100 microseconds pulses and here it is displayed without the 100 ms intervals between pulses. Two cases are shown: a trial in which successful irreversible electroporation was achieved and a case in which the voltage pulses apparently were not able to cause electroporation
Figure 21A:
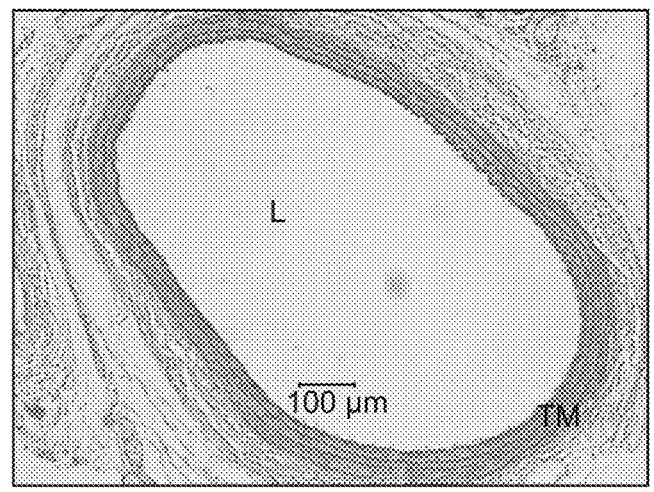
FIG. 21A is an actual photograph of a right common carotid artery of the device used in Example 1. This slide is an example of the appearance of a normal right carotid artery. (L—Intra-arterial lumen; TM—Tunica media).
Figure 21B:
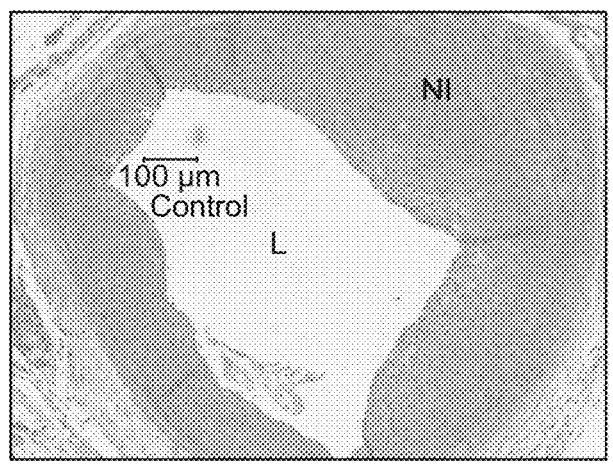
FIG. 21B is an actual photograph of a left common carotid artery 28 days after intimal damage, showing high neointima to media ratio. (L—Intra-arterial lumen; NI—Neointimal Formation) of the device used in Example 1.
Figure 21C:
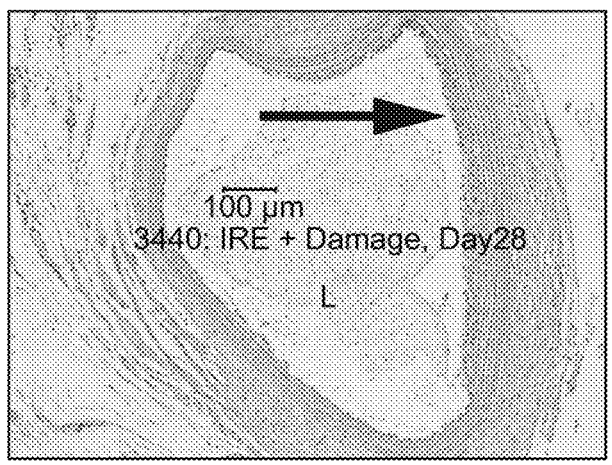
FIG. 21C is an actual photograph of a left common carotid artery 28 days after intimal damage in an IRE treated rat, showing the scarcity of neointimal formation compared with FIG. 21B (L—Intra-arterial lumen; Arrow—minimal neointimal formation) of the device used in Example 1.
Figure 22A:
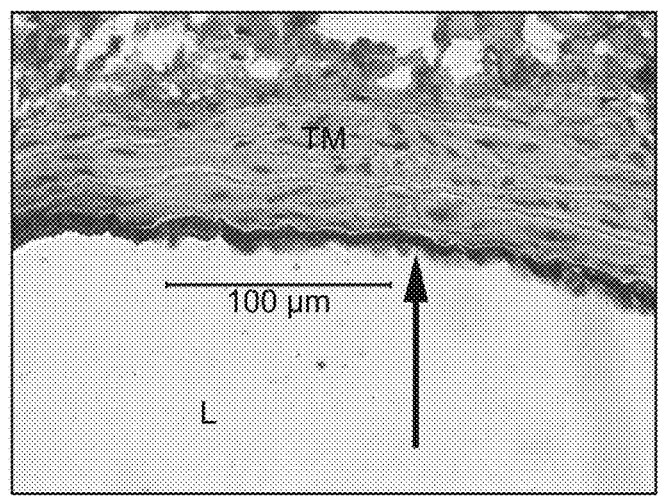
FIG. 22A is an actual photograph of a right common carotid artery. This slide is an example of the appearance of a normal control endothelial layer (L—Intra-arterial lumen; TM—Tunica media; Arrow—Endothelial layer) of the device used in Example 1.
Figure 22B:
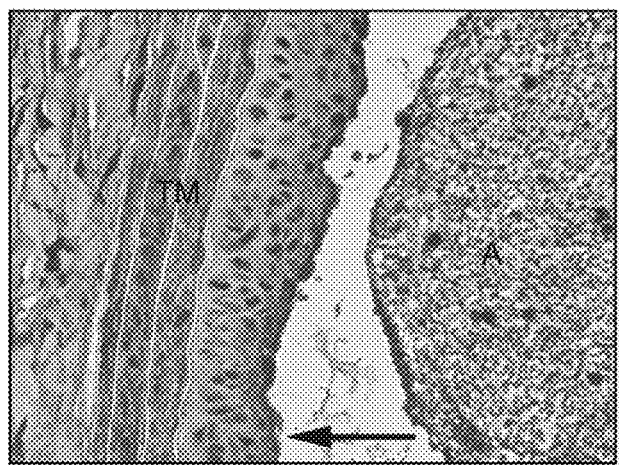
FIG. 22B is an actual photograph of a left common carotid artery, 28 days after intimal damage and IRE. This slide shows the overall preserved appearance of the endothelial layer. (A—Intra-arterial lumen artifact; TM—Tunica media; Arrow—Endothelial layer) of the device used in Example 1.
Figure 22C:
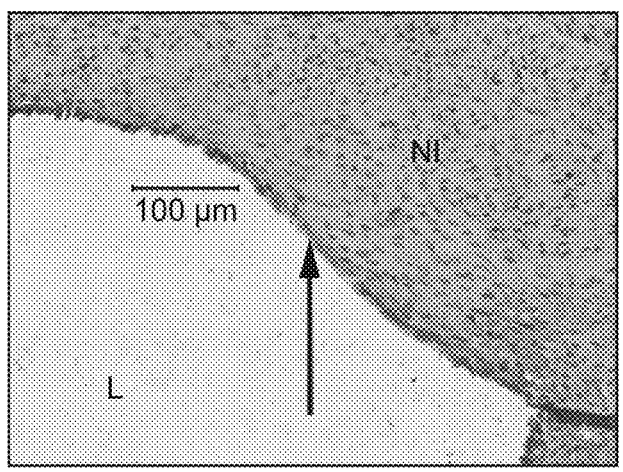
FIG. 22C is an actual photograph of a left common carotid artery, 28 days after intimal damage. This slide shows the damaged and irregular endothelial layer in the control group. (L Intra-arterial lumen; NI—Neointimal Formation; Arrow—irregular endothelial layer) of the device used in Example 1.
Figure 27:
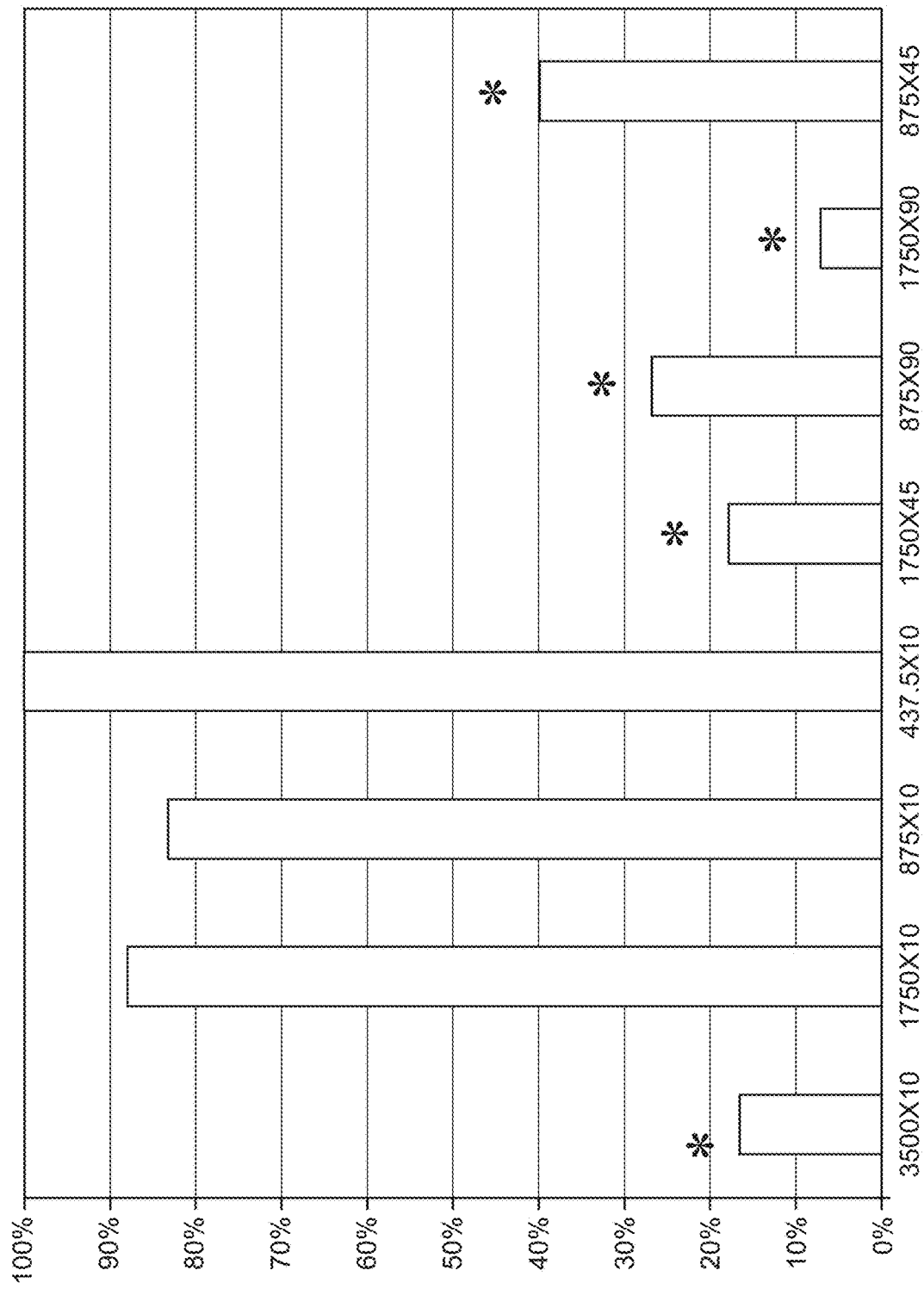
FIG. 27 is a bar graph showing the ablation effect due to different NTIRE protocols of Example 2. The reduction in five of the groups was statistically significant (P<0.001, bars marked with an asterisk). Ablation effect is shown as the percentage of VSMC cells in the treated artery compared with the right carotid artery of the same animal.

Once sufficient electrical energy has been delivered to the vessel wall 507, the balloon catheter 10 is deflated, causing distal collar 55 to move distally along the catheter shaft 19. The plurality of electrodes legs collapse against the deflating balloon 19 as shown in FIG. 17D. The device can then be removed from the patient (213). Cell death of the smooth muscle cells will occur within twenty-four hours of the electroporation treatment as illustrated by the absence of the endothelial layer 509 directly adjacent to the stenotic lesion 505 in FIG. 17D. The destroyed smooth muscle cells are subsequently removed by natural body processes (215). Extra-cellular structures of the vessel including the elastin/collegen base of the vessel wall are spared allowing the smooth muscle cells 509 to regenerate in a normal pattern. FIG. 17E illustrates the re-growth of a normal endothelial layer pattern across the stenotic region 505. Endothelial proliferation, which is triggered within hours of standard balloon angioplasty, is absent in the vessel treated with irreversible electroporation.

Since the voltage pulse generation pattern from the generator does not generate damaging thermal effect, and because the voltage pulses only ablate living cells, the treatment does not damage blood, blood vessel connective tissue or other non-cellular or non-living materials such as the catheter itself. The application of energy may be delivered to the vessel wall without damaging the balloon or other components of the catheter that might be damaged by temperatures created by a thermal therapy such as radiofrequency, laser, microwave or cryoplasty.

In another aspect of the invention, by periodically administering the electrical pulses according to a predetermined schedule, native stenotic lesions maybe prevented altogether.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Method

Eight Sprague-Dawley rats weighting 300-350 grams were used in this pilot study. All animals received humane care from a properly trained professional in compliance with both the Principals of Laboratory Animal Care and the Guide for the Care and Use of Laboratory Animals, published by the National Institute of Health (NIH publication No. 85-23, revised 1985).

Each animal was anaesthetized throughout the procedure. The left common carotid artery was exposed, and intimal denudation was performed as previously described. [Maor, et al. "The Effect of Irreversible Electroporation on Blood Vessels" *Technol Cancer Res Treat.* 6, 2007: 255-360; Touchard, et al. "Preclinical Restenosis Models: Challenges and Successes," *Toxicologic Pathology,* 34, pp. 2006: 11-18.] Briefly, the left external carotid artery was incised, and a 2F Fogarty arterial embolectomy catheter (Edwards Lifesciences) was advanced through the incision to the left common carotid artery. The balloon was inflated and drawn back three consecutive times. At the end of the procedure the balloon was deflated, extracted and the left external carotid artery was ligated.

Four rats were used as control, and their skin incision was sutured immediately at the end of the procedure. In the remaining four rats, a custom made electrode clamp with two parallel disk electrodes (diameter=5 mm) was applied on the left common carotid artery, very close to its bifurcation to the internal and external carotid arteries, at the exact site of intimal damage (see FIG. 1 for further details). The measured distance between electrodes was approximately 0.3 mm A sequence of 10 direct current pulses of 115 Volts (i.e. electrical field of approximately 3800 V/cm), 100 us each, at a frequency of 10 pulses per second, was applied between the electrodes using a high voltage pulse generator intended for electroporation procedures (ECM 830, Harvard Apparatus, Holliston, Mass.). Current and voltage were recorded by means of special oscilloscope probes (current probe was AP015 and high voltage probe was ADP305, both from LeCroy Corp.). From these two signals conductance was obtained during the pulses. The procedure was applied in three successive locations along the common carotid artery. At the end of the procedure the skin incision was sutured and animals were kept alive for a follow-up period of 28 days until they were euthanatized. Results obtained are shown in the table of FIG. 5.

Animals were euthanized with an overdose of Phenobarbital. The arterial tree was perfused with 10% buffered formalin for 40 minutes, and the left and right carotid arteries were exposed near the bifurcation of the internal and external carotid arteries. One slice of 1 cm from each artery, at the core of the treated area, was used for histological analysis. Each slice was fixed with 10% buffered formalin, embedded in paraffin, and sectioned with a microtome (5-µm-thick). One section was stained with hematoxylin and eosin. The endothelial layer was assessed by lectin immunostaining. Each slide was photographed at ×200 magnification, and the following areas were measured: tunica media area, neointimal area and lumen area. The unequal variance t-test method was used to evaluate the statistical difference between the measured areas of the two different groups.

Results

All animals survived the procedures. Conductance of the arterial wall decreased during successive direct current pulses (FIG. 2a). During the follow-up period there were no signs of cerebrovascular events (paraplegia, paraparesis, etc.) and there was no mortality.

Conductance was measured during IRE pulses and was used to monitor the successful use of the electroporation device. Successful IRE was assigned to those cases in which significant conductance increase was observed during applied pulses, as depicted in the case shown in FIG. 2. IRE was successful in 3 of the 4 animals. There were no changes in conductance during the pulses applied to the fourth animal and this was considered to indicate unsuccessful IRE (see also FIG. 2). A constant observation in all successful IRE cases was that, despite conductance increased during each pulse, the overall conductance for the whole sequence decreased.

After 28 days, histological analysis was used to compare the IRE-treated and the control group (FIG. 3). Measurements of neointimal area, tunica media area and arterial lumen area are summarized in Table 1. Compared with control (including the one unsuccessful IRE animal), successful IRE induced a significant reduction in the neointima to media ratio (0.57±0.4 vs. 1.88±1.0, P=0.02). In addition, compared with control (excluding the unsuccessful IRE animal), successful IRE induced a reduction in neointimal to media ratio that was less significant (0.57±0.4 vs. 1.67±1.0, P=0.06).

Examples of the endothelial layer in the different animals are shown in FIG. 3. Endothelial layer seems to have well recovered in the IRE-treated animals compared with control group animals. Endothelial integrity was similar in the IRE-treated group to its appearance in the unharmed right common carotid artery (FIG. 4).

Discussion

The results demonstrate the ability of IRE to reduce restenosis. There was reduced neointimal formation following successful IRE, compared with control animals. Based on histological analysis, the extra cellular matrix component of the arterial wall was maintained; there was no evidence of necrosis, aneurysm formation, or thrombosis, and there was remarkable recovery of the endothelial layer. Thermal damage to this layer was avoided.

Atherosclerosis, arterial remodeling and restenosis following angioplasty are complex processes, in which the arterial wall in general, and the vascular smooth muscle cells in particular, play a role. [Ward, et al. "Arterial Remodeling: Mechanisms and Clinical Implications," *Circulation.* 102, 2000: 1186-1191; Davies, et al. "Pathobiology of intimal hyperplasia," *Br J Surg.* 81, 1994: 1254-69; Lusis, et al. "Atherosclerosis," *Nature.* 407, 2000: 233-241.]

Results provided here show that compared with non-IRE treated controls, there is significant decrease in neointimal formation 28 days after intimal damage in IRE-treated arteries. In a previous study we showed that in the same model, IRE induced significant reduction in the VSMC population without apparent damage to elastic fibers. [Maor, et al. "The Effect of Irreversible Electroporation on Blood Vessels" *Technol Cancer Res Treat.* 6, 2007: 255-360.] Clarke et al. ["Apoptosis of vascular smooth muscle cells induces features of plaque vulnerability in atherosclerosis," *Nat Med.* 12, 2006: 1075-1080] investigated the role of VSMC per se in vascular disease. Using transgenic mice expressing human diphtheria toxin receptor on all VSMCs, they showed that apoptosis of 50-70% of the VSMC population in normal arteries induced no endothelial loss, inflammation, reactive proliferation, thrombosis, remodeling or plaque formation.

The results provided here show that by selectively destroying the VSMC population without affecting the extracellular matrix, the specific non-thermal IRE ablation method described here significantly reduces the potential ability of neointimal formation, without significant damage to arterial function and overall structure.

To date, different methods to ablate or stop the proliferation of cells in the different layers of the arterial wall have been suggested. These methods include cryoplasty, brachytherapy, photodynamic therapy, drug-eluting stents and genetic manipulations using gene therapy. [Tanguay, et al.

"Percutaneous endoluminal arterial cryoenergy improves vascular remodelling after angioplasty," *Thromb. Haemost.* 92, 2004: 1114-1121; Yiu, et al. "Vascular Smooth Muscle Cell Apoptosis Induced by 'Supercooling' and Rewarming" *J Vasc Intery Radiol.* 17, 2006: 1971-1977; Fava, et al. "Cryoplasty for Femoropopliteal Arterial Disease: Late Angiographic Results of Initial Human Experience," *J Vasc Intery Radiol.* 15, 2004: 1239-1243; Laird, et al. "Cryoplasty for the Treatment of Femoropopliteal Arterial Disease: Results of a Prospective, Multicenter Registry," *J Vasc Intery Radiol.* 16, 2005: 1067-1073; Samson, et al. "Cryo-Plasty Therapy of the Superficial Femoral and Popliteal Arteries: A Single Center Experience," *Vasc. Endovascular Surg.* 40, 2007: 446-450; Lagerqvist, et al. "Long-Term Outcomes with Drug-Eluting Stents versus Bare-Metal Stents in Sweden," *N Engl J Med.* 356, 2007: 1009-1019; Leon, et al. "Localized Intracoronary Gamma-Radiation Therapy to Inhibit the Recurrence of Restenosis after Stenting," *N Engl J Med.* 344, 2001: 250-256; Waksman, et al. "Two-year follow-up after beta and gamma intracoronary radiation therapy for patients with diffuse in-stent restenosis," *Am. J. Cardiol.* 88, 2001: 425-428; Teirstein, et al. "New Frontiers in Interventional Cardiology: Intravascular Radiation to Prevent Restenosis," *Circulation.* 104, 2001: 2620-2626; Salame, et al. "The Effect of Endovascular Irradiation on Platelet Recruitment at Sites of Balloon Angioplasty in FIG. Coronary Arteries," *Circulation.* 101, 2000: 1087-1090; Cheneau, et al. "Time Course of Stent Endothelialization After Intravascular Radiation Therapy in Rabbit Iliac Arteries," *Circulation.* 107, 2003: 2153-2158; Waksman, et al. "Intracoronary photodynamic therapy reduces neointimal growth without suppressing re-endothelialisation in a porcine model," *Heart.* 92, 2006: 1138-1144; Mansfield, et al. "Photodynamic therapy: shedding light on restenosis." *Heart.* 86, 2001: 612-618; Stone, et al. "A Polymer-Based, Paclitaxel-Eluting Stent in Patients with Coronary Artery Disease," *N Engl J Med.* 350, 2004: 221-231; Moses, et al. "Sirolimus-Eluting Stents versus Standard Stents in Patients with Stenosis in a Native Coronary Artery," *N Engl J Med.* 349, 2003: 1315-1323; Makinen, et al. "Increased Vascularity Detected by Digital Subtraction Angiography after VEGF Gene Transfer to Human Lower Limb Artery: A Randomized, Placebo-Controlled, Double-Blinded Phase II Study," *Mol Ther.* 6, 2002: pp. 127-133; Hedman, et al. "Safety and Feasibility of Catheter-Based Local Intracoronary Vascular Endothelial Growth Factor Gene Transfer in the Prevention of Postangioplasty and In-Stent Restenosis and in the Treatment of Chronic Myocardial Ischemia. Phase II Results of the Kuopio Angiogenesis Trial (KAT)," *Circulation.* 2003: 01.]

The IRE methodology disclosed and described here is different from and has advantages over these other methods for reducing restenosis. The nature of the IRE mechanism alone is to produce only nanoscale defects in the cell membrane. [Chen, et al. "Membrane electroporation theories: a review." *Med Biol Eng Comput.* 44, 2006: 5-14.] In the absence of thermal damage, IRE does not affect connective tissue, the extracellular matrix, nor does it denaturizes proteins. [Maor, et al. "The Effect of Irreversible Electroporation on Blood Vessels." *Technol Cancer Res Treat.* 6, 2007: 255-360; Lee, et al. "Distinguishing Electroporation from Thermal Injuries in Electrical Shock By MR Imaging." *Conf Proc IEEE Eng Med Biol Soc.* 6, 2005: 6544-6546.] Therefore, the integrity of the extracellular matrix is retained during the process. The extra-cellular matrix plays an important role in arterial remodeling and in the elastic properties of the arterial wall. [Li, et al. "Elastin is an essential determinant of arterial morphogenesis," *Nature.* 393, 1998: 276-280.] One explanation for the absence of aneurysm formation in accordance with the present invention may be that IRE does not damage elastin or collagen within the arterial wall. One of the problems with an intra-arterial stent is the intense extra cellular formation in the later stages of restenosis, probably due to the mechanical damage caused by the stent. [Chung, et al. "Enhanced extracellular matrix accumulation in restenosis of coronary arteries after stent deployment," *J Am Coll Cardiol.* 40, 2002: 2072-2081.] Because electrical fields can either produce IRE or not, without any gradual modalities of damage, the margins of the treated region are well delineated and do not extent beyond the area of application of the IRE field. Therefore, with IRE the effect can be achieved only in the area of interest, without collateral damage. The use of the IRE method of the present invention is a non-pharmacological method, and therefore there is less concern regarding allergic reaction or drug safety.

IRE, and electroporation in general, produces nano-scale defects in the cell membrane and thereby facilitates unimpeded ion transport across the membrane. [Chen, et al. "Membrane electroporation theories: a review." *Med Biol Eng Comput.* 44, 2006: 5-14.] Therefore, successful IRE results in immediate changes in the passive electrical properties of the tissue that can be measured and employed as a feedback mechanism for real time control of the technique. In fact, within the context of reversible electroporation, such strategy has been described previously for individual cells [Huang et al. "Micro-electroporation: improving the efficiency and understanding of electrical permeabilization of cells," *Biomed. Microdevices.* 3, 1999: 145-150], cell cultures [Pavlin, et al. "Effect of Cell Electroporation on the Conductivity of a Cell Suspension," *Biophys. J.* 88, 2005: 4378-4390] and tissues. [Davalos, et al. "A Feasibility Study for Electrical Impedance Tomography as a Means to Monitor Tissue Electroporation for Molecular Medicine," *IEEE Trans. Biomed. Eng.* 49, 2002: 400-403; Cukjati, et al. "Real time electroporation control for accurate and safe in vivo non-viral gene therapy," *Bioelectrochemistry.* 70, 2007: 501-507.]

A common, and expected, observation in previous studies in which in vivo conductance has been measured during the application of a sequence of high voltage pulses, either for reversible or for irreversible electroporation [Ivorra, et al. "In vivo electrical impedance measurements during and after electroporation of rat liver," *Bioelectrochemistry.* 70, 2007: 287-295; Payselj, et al. "The course of tissue permeabilization studied on a mathematical model of a subcutaneous tumor in small animals," *IEEE Trans. Biomed. Eng.* 52, 2005: 1373], is that electrical conductance increases during the sequence and not only within the pulses. The only exception seems to be the skeletal muscle under IRE. In that particular case, conductance measured at the pulses is quite constant during the whole sequence. In accordance with the methodology of the present invention, conductance decreases during the sequence of pulses. With the understanding that we are not bound to a particular theory or explanation, we believe that a plausible hypothesis is that IRE pulses cause contraction of the arteries [Jackson, et al. "Regional variation in electrically-evoked contractions of rabbit isolated pulmonary artery," *Br J Pharmacol.* 137, 2002: 488-496] and that such contraction results in an increase of the impedance of the arteries, particularly of the smooth muscle tissue. [Liao, et al. "The Variation of Action Potential and Impedance in Human Skeletal Muscle during Voluntary Contraction," *Tohoku J. Exp. Med.* 173, 1994:

303-309; Shiffman, et al. "Electrical impedance of muscle during isometric contraction," *Physiol. Meas.* 24, 2006: 213-234.]

The results provided here show a failure to induce IRE in one of the animals. This may have been caused by not applying the electrodes properly to the artery so that the resulting electrical contact was not good enough over the artery. Direct short-circuiting of the electrodes or through plasma or saline solution does not seem plausible because it would have caused larger conductivity than the measured conductivity during the pulses (FIG. 2).

Successful IRE depends on parameters such as electric field magnitude, pulses length and frequency. The reason for choosing the particular electrical parameters used in this study are consistent with the mode of application of IRE of the present invention. These are electrical parameters that were assessed to be high enough to ensure irreversible electroporation [Davalos, et al. "Tissue Ablation with Irreversible Electroporation," *Ann. Biomed. Eng.* 33, 2005: 223-231; Edd, et al. "In vivo results of a new focal tissue ablation technique: irreversible electroporation." *IEEE Trans Biomed Eng.* 53, 2006: 1409-15; Miller, et al. "Cancer Cells Ablation with Irreversible Electroporation," *Technol Cancer Res Treat.* 4, 2005: 699-705; Rubinsky, "Irreversible electroporation in medicine." *Technol. Cancer Res* Treat. 6. 2007: 255-60; Rubinsky, et al. "Irreversible electroporation: a new ablation modality—clinical implications." *Technol Cancer Res Treat.* 6, 2007: 37-48; Ivorra, et al. "In vivo electrical impedance measurements during and after electroporation of rat liver," *Bioelectrochemistry.* 70, 2007: 287-295; Maor, et al. "The Effect of Irreversible Electroporation on Blood Vessels" *Technol Cancer Res Treat.* 6, 2007: 255-360; Touchard, et al. "Preclinical Restenosis Models: Challenges and Successes," *Toxicologic Pathology,* 34, pp. 2006: 11-18; Dev, et al. "Intravascular Electroporation Markedly Attenuates Neointima Formation After Balloon Injury of the Carotid Artery in the Rat." *J Interven Cardiol.* 13, 2000: 331-338] but which do not cause damaging levels of Joule heating. We used a sequence of 10 direct current pulses of 115 Volts (i.e. electrical field of approximately 3800 V/cm), 100 μs each, at a frequency of 10 pulses per second. These parameters where partially based on previous reports that showed successful tumor cell ablation with IRE. [Miller, et al. "Cancer Cells Ablation with Irreversible Electroporation," *Technol Cancer Res Treat.* 4, 2005: 699-705; Rubinsky, et al. "Irreversible electroporation: a new ablation modality—clinical implications." *Technol Cancer Res Treat.* 6, 2007: 37-48; Al-Sakere, et al. "Tumor Ablation with Irreversible Electroporation." *PLoS ONE.* 2, 2007: e1135.] Since the arterial wall has different morphology, and since we did not have data regarding the specific susceptibility of vascular smooth muscle cells to IRE, we used an electrical field that was higher than any previous report but low enough not to produce thermal damage within the constraints of the treated tissue dimensions. Those skilled in the art will be able to follow the results provided here to show the relation between conductance measurements during the procedure and IRE efficiency.

The examples described here used rodent carotid artery model. This model is an acceptable animal model of restenosis [Touchard, et al. "Preclinical Restenosis Models: Challenges and Successes," *Toxicologic Pathology,* 34, pp. 2006: 11-18; Narayanaswamy, et al. "Animal Models for Atherosclerosis, Restenosis, and Endovascular Graft Research," *J Vasc Intery Radiol.* 11, 2000: 5-17], but it is important to clarify that our experiments were performed on arteries that were not atherosclerotically changed. However, we believe these results can be readily applied to humans to show the efficacy of IRE in atherosclerotically changed arteries.

Our electrodes were clamping the artery on its outer surface, but this does not imply that this method will be used as an invasive procedure. Previous reports have already demonstrated the ability to design and use intra-vascular devices in order to induce reversible electroporation of the arterial wall. [Dev, et al. "Intravascular Electroporation Markedly Attenuates Neointima Formation After Balloon Injury of the Carotid Artery in the Rat." *J Interven Cardiol.* 13, 2000: 331-338.] Those skilled in the art will understand that similar designs can be used to achieve IRE on humans using intra-vascular devices.

The invention provides in vivo, long-term results of a new non-thermal, non-pharmacological strategy to attenuate neointimal formation following intimal damage. Importantly, the invention provides for the treatment of restenosis following coronary angioplasty and the delivery of that treatment with real time control.

The method of the invention can be used in preventing and/or ablating coronary and peripheral restenosis process, while also playing a role in attenuating atherosclerotic processes in clinically important locations, such as coronary, carotid and renal arteries.

Example 2

Summary of Method and Results

33 Sprague-Dawley rats were used to compare NTIRE protocols. Each animal had NTIRE applied to its left common carotid using custom-made electrodes. The right carotid artery was used as control. Electric pulses of 100 microseconds were used. Eight IRE protocols were compared: 1-4) 10 pulses at a frequency of 10 Hz with electric fields of 3500, 1750, 875 and 437.5 V/cm and 5-8) 45 and 90 pulses at a frequency of 1 Hz with electric fields of 1750 and 875 V/cm. Animals were euthanized after one week. Histological analysis included VSMC counting and morphometry of 152 sections. Selective slides were stained with elastic Van Gieson and Masson trichrome to evaluate extracellular structures. Most efficient protocols were 10 pulses of 3500 V/cm at a frequency of 10 Hz and 90 pulses of 1750 V/cm at a frequency of 1 Hz, with ablation efficiency of 89±16% and 94±9% respectively. Extra-cellular structures were not damaged and the endothelial layer recovered completely.

Summary Conclusion

NTIRE is a promising, efficient and simple novel technology for VMSC ablation. It enables ablation within seconds without causing damage to extra-cellular structures, thus preserving the arterial scaffold and enabling endothelial regeneration. This study provides scientific information for future anti-restenosis experiments utilizing NTIRE.

Method

Thirty three Sprague-Dawley rats weighting 160-280 grams were used in this study. All animals received humane care from a properly trained professional in compliance with both the Principals of Laboratory Animal Care and the Guide for the Care and Use of Laboratory Animals, published by the National Institute of Health (NIH publication No. 85-23, revised 1985).

Animals were anaesthetized with an intramuscular injection of Ketamin and Xylazine (90 mg/Kg and 10 mg/Kg, respectively). The left common carotid artery of each animal was exposed and a custom made electrode clamp with two parallel disk electrodes was applied on the left common carotid artery as previously described. (Maor E, Ivorra A, Leor J, Rubinsky B. Irreversible Electroporation Attenuates Neointimal Formation After Angioplasty. *Biomedical Engineering, IEEE Transactions* on. 2008; 55(9):2268-2274) The custom made electrode clamp consists of two printed circuit boards (1.5 mm thickness) with disk electrodes (diameter=5 mm) made of copper (70 μm thickness) plated with gold (manufacturing process by Sierra Proto Express, Sunnyvale, Calif.).

Animals were divided to eight different groups (FIG. 24). All groups had their left common carotid artery treated with NTIRE and their right common carotid artery used as a control. NTIRE was performed by applying short electric pulses between the electrodes using a high voltage pulse generator intended for electroporation procedures (ECM 830, Harvard Apparatus, Holliston, Mass.). Current and voltage were recorded by means of special oscilloscope probes (current probe was AP015 and high voltage probe was ADP305, both from LeCroy Corp.). From these two signals conductance (defined as current/voltage) was obtained for each pulse (mean value of the last 10 μs of the pulse). The procedure was repeated in three successive locations along the common carotid artery, thus treating approximately 1.5 cm of the left common carotid artery. At the end of the procedure the skin incision was sutured closed and the animals were kept alive for a follow-up period of 7 days.

All pulses were 100 μs in length. The number of pulses, the applied electric field, and the frequency of the pulses differed between the groups as summarized in FIG. 24.

Histological Assessment

Animals were euthanized with an overdose of Phenobarbital followed by bilateral chest dissection. Gross inspection of carotid arteries was used to identify arterial wall integrity or intraluminal massive thrombus formation. The arterial tree was perfused with 10% buffered formalin, and the left and right carotid arteries were harvested near the bifurcation of the internal and external carotid arteries. The treated area was cut to two or three consecutive slices. One section from each slice was used for histological analysis. Each slice was fixed with 10% buffered formalin, embedded in paraffin, and sectioned with a microtome (5-μm-thick). Sections were stained with hematoxylin and eosin. Each section was photographed at ×200 magnification, and the following parameters were quantitatively evaluated: number of VSMC nuclei in each of the three layers of the Tunica Media, total area of the Tunica Media, and the average thickness of the Tunica Media based on 5 different measurements in each section. VSMC concentration was calculated by dividing the total number of nuclei by the measured area of the Tunica Media. The paired t-test method was used to evaluate the statistical difference between the measured areas of the control versus IRE-treated groups.

In addition, selected sections were stained with elastic Van Gieson (EVG) and Masson trichrome in order to evaluate the extra-cellular elastic and collagen fibers, respectively Immunostaining with CD31 and CD34 antibodies (Pathology Services Inc., Berkeley, Calif.) was used to evaluate the endothelial layer.

Results

All 33 animals survived the procedure. During follow-up period, there were no cases of infection, bleeding at IRE-treated arteries, thrombosis or animal mortality.

NTIRE VSMC Ablation Efficiency

Figure 28:
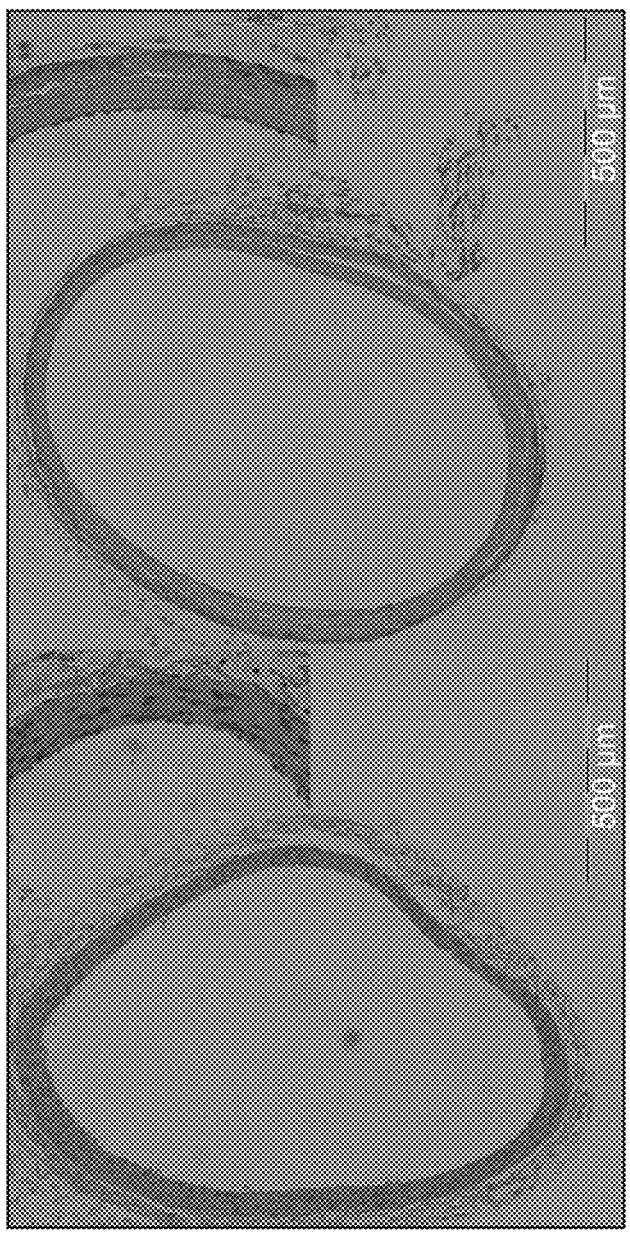
FIG. 28 is an actual photograph showing complete ablation of VSMC population of Example 2 one week following NTIRE with 90 pulses of 1,750 V/cm (right picture) compared with right carotid artery of the same animal that was used as a control (left picture). Note the complete absence of VSMC cells compared with notable repopulation of the endothelial layer with endothelial cells.
Figure 30:
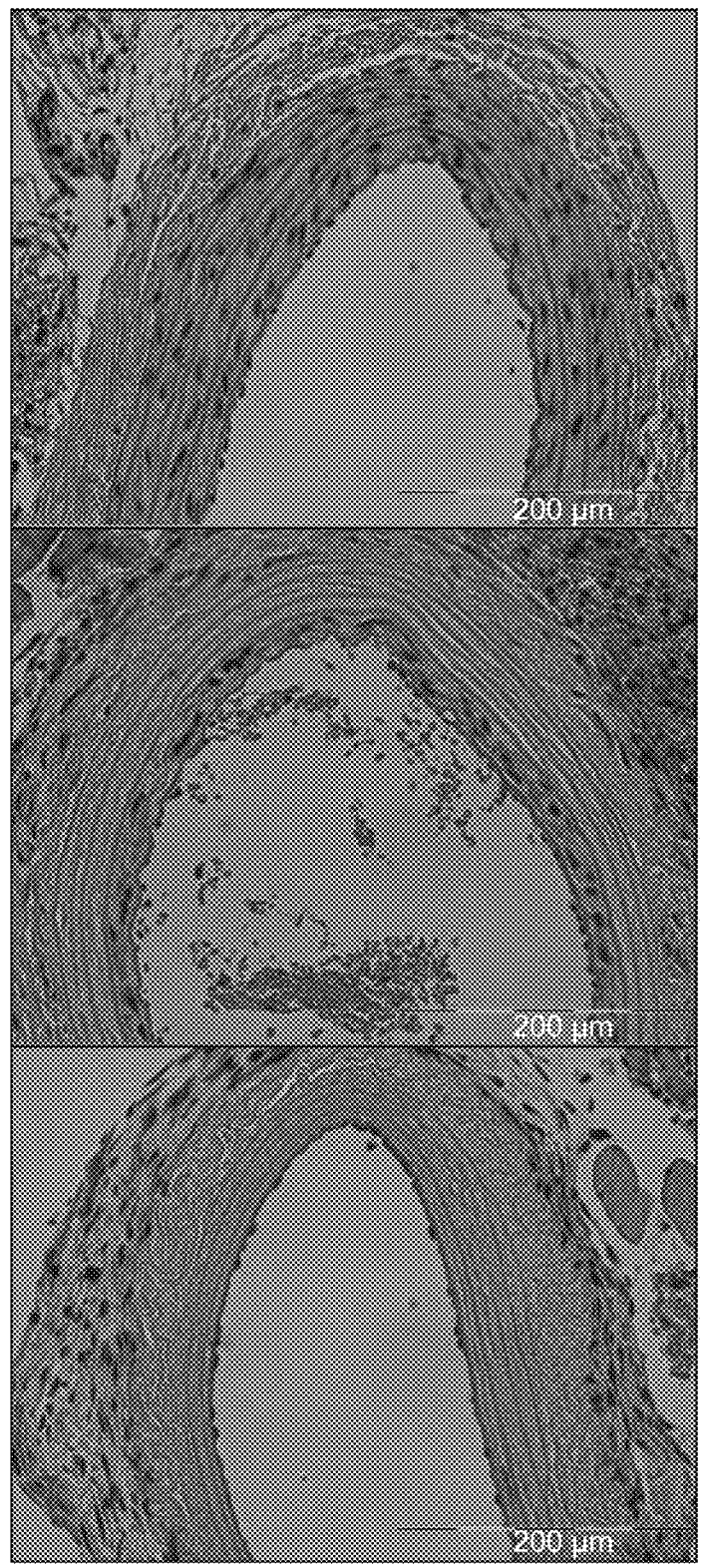
FIG. 30 consists of FIGS. 30A, 30B and 30c which are three actual photographs taken at magnification (×40) of the effect of NTIRE on blood vessels after one week of Example 2. Top picture (30A) shows a control artery, middle picture (30B) shows a partial effect due to 45 pulses of 875 V/cm (Group 6), lower picture (30C) shows a complete ablation of the arterial VSMC population. In the case of the partial effect—all surviving VSMC are located in the innermost layer of the Tunica Media. Also, note in the lower picture the repopulation of the endothelial layer with endothelial cells, compared with total absence of VSMC.

Results of all eight groups are summarized in FIGS. 25 and 26. Best NTIRE ablation results were achieved in Groups 1 and 7 (FIG. 24). Group 1 had 89±16% reduction in the number of VSMC compared with control (24±34 vs. 208±40, $P<0.001$) and Group 7 had 94±9% reduction in the number of VSMC compared with control (13±21 vs. 213±33, $P<0.001$). An example of complete ablation of the entire arterial wall is shown in FIGS. 28 and 30.

While ten pulses of 3,500 V/cm were efficient, ten pulses of lower electric fields had a minor ablation effect (1,750 V/cm, group 2: 167±66 vs. 214±38, $P=0.05$) or no effect at reducing VSMC population (Groups 3 & 4, 875 and 437.5 V/cm respectively). Increasing the number of pulses with electric field of 1,750 V/cm improved the ablation efficiency (VSMC population reduction of 22±30%, 86±16% and 94±9% with 10, 45 and 90 pulses respectively). Similar trend of increasing efficiency was also apparent with an electric field of 875 V/cm (63±29% and 79±17% with 45 and 90 pulses, respectively), but efficiency values were not high enough even with 90 pulses (49±40 vs. 236±31, $P<0.001$).

Figure 29:
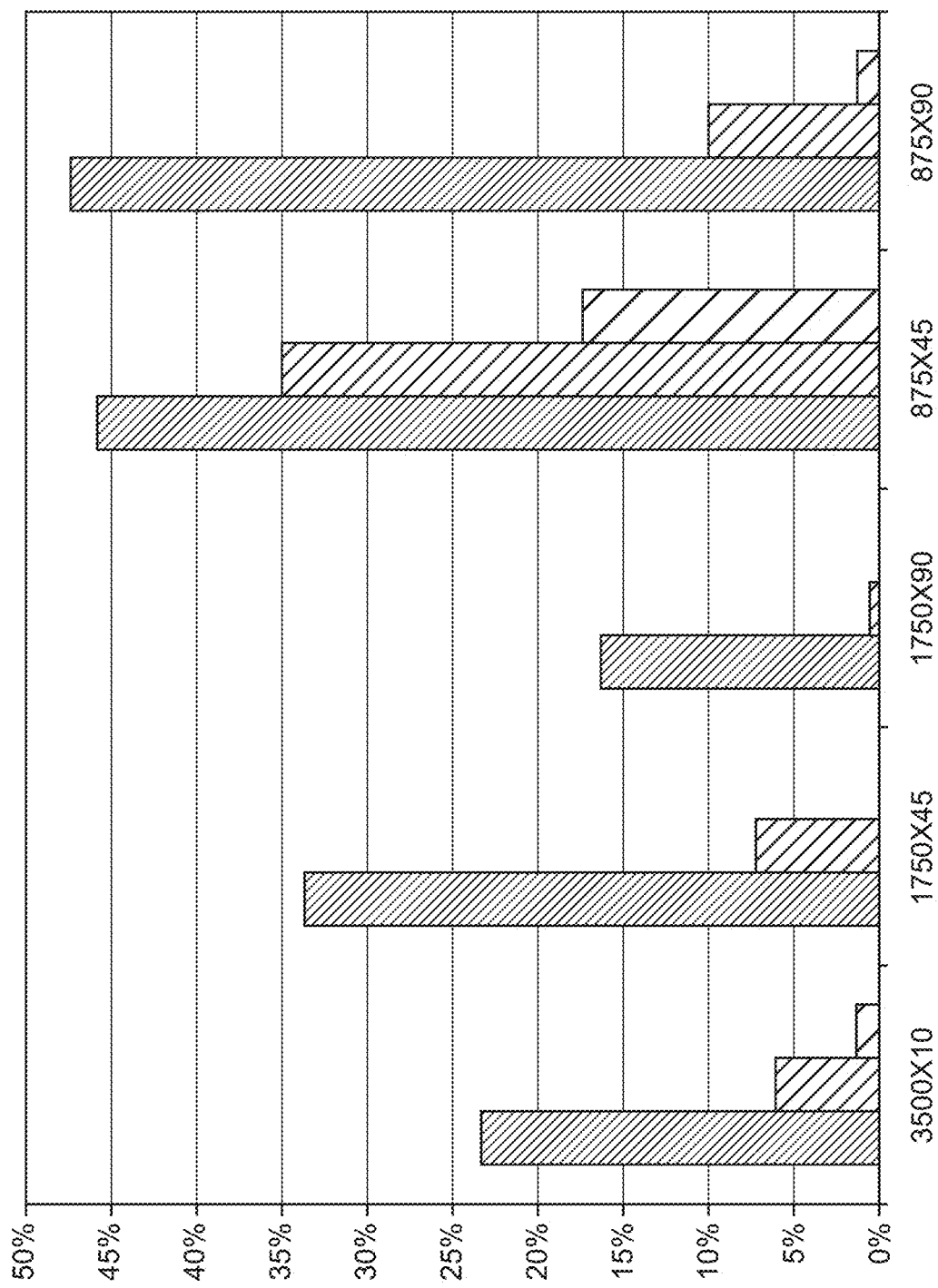
FIG. 29 is a bar graph showing the effect on the sub-layer of the Tunica Media of Example 2. Inner most, middle and outer sub-layers are in the first, second and third positions, left to right, respectively. Ablation effect is shown as the percentage of VSMC cells in the sub-layer compared with the same sub-layer in the right carotid artery of the same animal. Note the relative sparing of the inner most VSMC cells in all five groups, compared with the complete ablation of VSMC in the outer layers with 1750 V/cm (second and third groups in FIG. 29).

Sub-analysis of ablation efficiency at the three separate layers of the Tunica Media showed that the best results were achieved in the outer layers of the Tunica Media, and most VSMC that survived NTIRE were located in the inner most layer (FIG. 29). For example, in the case of Group 7, no VSMC nuclei could be located in the outer layer in all sections evaluated. All 6% surviving VSMC in this group were located in the inner layer of the Tunica Media (FIG. 30).

Figure 31:
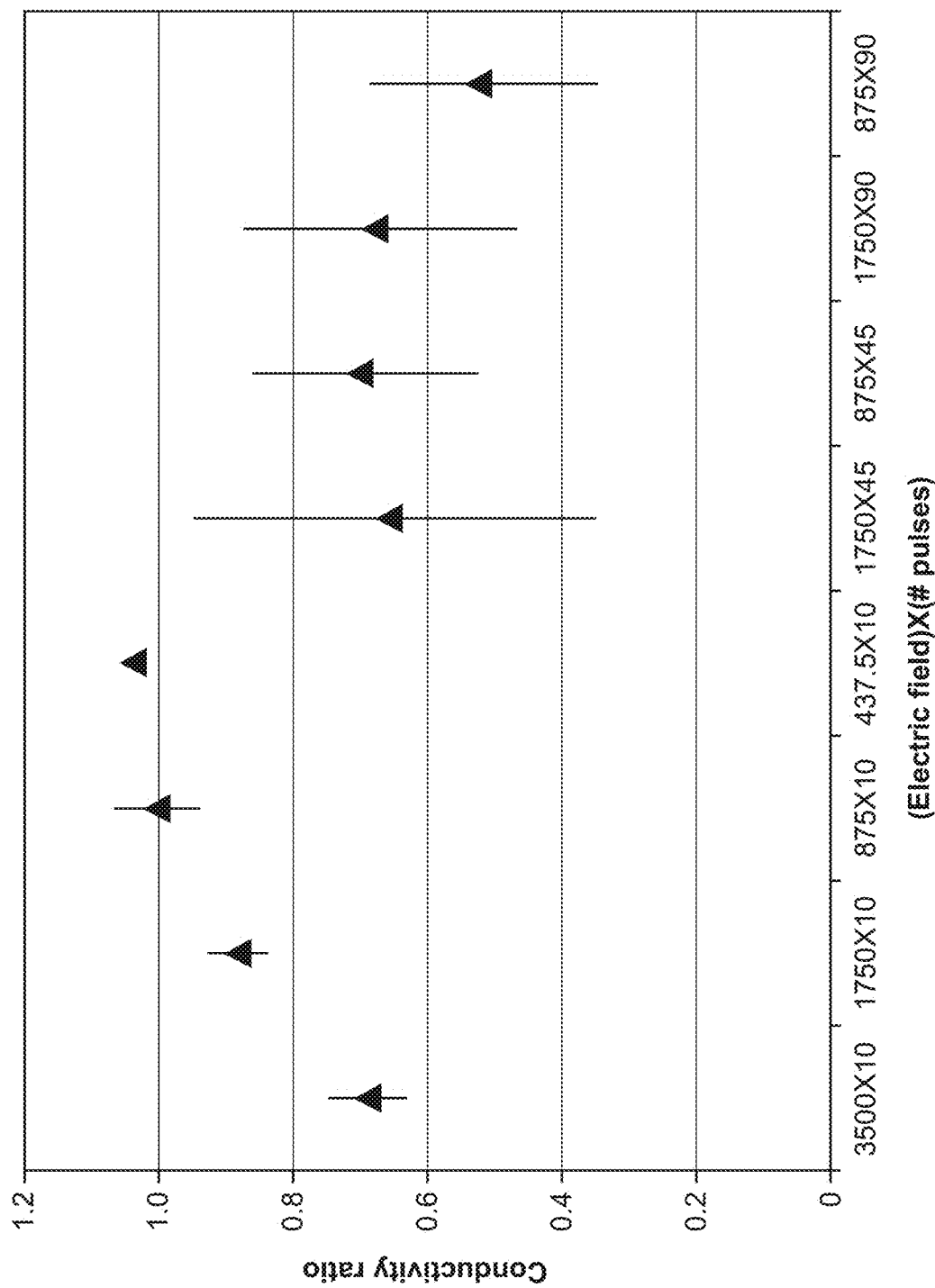
FIG. 31 is a graph showing the conductance change during NTIRE application. X-axis shows the eight study groups of Example 2. Y-axis shows the change as the ratio between the conductance value measured at the last electroporation pulse and the value at the first pulse. Groups 3 and 4 (875×10 and 437.5×10, respectively) show no change in conductivity, which correlates well with the no ablation effect (see FIG. 28). Group 2 (1,750×10) shows partial reduction in conductivity, correlating well with minor ablation effect.

Electric conductance changed during the application of NTIRE (FIG. 31). The conductance measured during the last pulse was lower compared with conductance measured during the first pulse in all groups except Groups 3 & 4 (two groups with no significant NTIRE ablation effect). For the most effective protocols, conductance was reduced by 31±6% and 32±20% for Groups 1 and 7, respectively.

NTIRE Effect on other Arterial Wall Components

Successful NITRE ablation of VSMC induced a reduction in media thickness: 25±17% reduction in group 1 (45±10 vs. 59±8 μm) and 27±7% reduction in Group 7 (37±4 vs. 51±6 μm). No change in media thickness was induced in the two non-successful NTIRE groups (61±9 vs. 58±7 μm in Group 3, 61±9 vs. 60±6 μm in Group 4).

Endothelial cells of treated arteries were similar in number and morphology to those of non treated control arteries, but were negative to both CD31 and CD34 antibodies (data shown only for CD34 staining, see bottom row in FIG. 32). EVG stain demonstrated intact elastic fibers and preserved vessel wall, similar to that of control arteries (middle row, FIG. 32). Masson Trichrome stain demonstrated minor fibrosis in perivascular areas, with collagen being the dominant component of the Tunica Media following the complete loss of VSMC population (top row, FIG. 32).

Discussion

This is the first large scale, in-vivo survival experiment to evaluate and compare the effect of different NTIRE protocols on VSMC population. The results show that NTIRE can achieve efficient ablation of VSMC within seconds, without damaging extra-cellular components.

Current study results are supported by previous studies by our group. In a preliminary study evaluating NTIRE effect on blood vessels, a 87% reduction in VSMC concentration after 28 days was observed following NTIRE with similar parameters to those of Group 1 (10 pulses, 100 μsec, 10 Hz, 3800 V/cm). (Maor E, Ivorra A, Leor J, Rubinsky B. The Effect of Irreversible Electroporation on Blood Vessels. *Technology in Cancer Research and Treatment.* 2007; 6(4): 255-360) Parameters similar to Group 1 have also been shown to significantly reduce neointimal formation following angioplasty in rodent carotid injury model. (Maor E, Ivorra A, Leor J, Rubinsky B. Irreversible Electroporation Attenuates Neointimal Formation After Angioplasty. *Biomedical Engineering, IEEE Transactions on.* 2008; 55(9): 2268-2274).

Our results are also supported by the work of Al-Sakere et al. (Al-Sakere B, André F, Bernat C, et al. Tumor Ablation with Irreversible Electroporation. *PLoS ONE.* 2007; 2(11): e1135) In their in-vivo study with sarcoma tumor, best tumor ablation using irreversible electroporation was achieved with the use of 80 electroporation pulses of 100 μs at 0.3 Hz with an electrical field magnitude of 2,500 V/cm. Their most efficient protocol was the one with the largest number of pulses and the highest electric field evaluated, similar to the results presented here. Based on these results, it seems that irreversible electroporation is limited only by the joule heating effect. As long as there is no thermal damage to extra-cellular structures, increase in electric field magnitude and pulse number will be translated to larger ablation volume and better ablation efficiency.

For Groups 1 and 7, where best ablation efficiency was observed, around 10% of the VSMC population survived the ablation. Further analysis of the results demonstrated 100% efficiency in the outer layers of the Tunica Media, with all surviving cells located in the inner most layers of the arterial wall (FIGS. 29 and 30). The most probable explanation for this phenomenon is the nature of the electric field. We assumed uniform electric field between the two electrodes, but since the arterial tissue is not homogeneous with respect to its electric properties, the actual electric field in the inner most area of the artery might have been lower than expected. A better design with a more uniform electric field might allow NTIRE to achieve higher ablation efficiencies compared with those reported in this study. Another plausible explanation is the proximity of surviving cells to the oxygenated blood of the carotid artery. The availability of oxygen and nutrient might have a protective effect that reduces the vulnerability of these cells to the stress insult caused by the damage to the cell's membrane.

Our results show that reduction of the electric field magnitude can be compensated by increasing the number of NTIRE pulses. Ten pulses of 3500 V/cm achieved similar effect to 90 pulses of 1750 V/cm. However, decreasing the electric field even more to 875 V/cm caused a decrease in NTIRE efficiency even with the use of 90 pulses. This observation may be important in future NTIRE device designs, where intervention time could be reduced by increasing trans-electrode electric potential.

A common observation in previous electroporation studies, either reversible or irreversible, is that electrical conductance measured at the pulses increases during the sequence of pulses. (Ivorra A, Miller L, Rubinsky B. Electrical impedance measurements during electroporation of rat liver and muscle. In: 13*th International Conference on Electrical Bioimpedance and the* 8*th Conference on Electrical Impedance Tomography.;* 2007:130-133. Available at: http://dx.doi.org/10.1007/978-3-540-73841-1_36 [Accessed Oct. 21, 2008]) The only exception to this seems to be for skeletal muscle under NTIRE. (Ivorra A, Miller L, Rubinsky B. Electrical impedance measurements during electroporation of rat liver and muscle. In: 13*th International Conference on Electrical Bioimpedance and the* 8*th Conference on Electrical Impedance Tomography.;* 1_2007:130-133. Available at: http://dx.doi.org/10.1007/978-3-540-73841-1_36) In that particular case, conductance measured at the pulses remains quite constant during the whole sequence and it can be explained as a saturation effect of the electroporation phenomenon. However, the fact that conductance decreases during the sequence is quite surprising as it contradicts what would be expected in a simple electroporation model: electroporation increases cell membrane permeability to ions and therefore its conductance should also increase. We do not have a definitive explanation for the conductance decrease observed here. We consider that a plausible hypothesis is that NTIRE pulses cause a contraction of the arteries by stimulating the vascular smooth muscle cells and that such a contraction results in an increase in the electrical impedance of the arteries. (Liao T J, Nishikawa H. The variation of action potential and impedance in human skeletal muscle during voluntary contraction. *Tohoku J Exp Med.* 1994; 173(3):303-9; Shiffman C A, Aaron R, Rutkove S B. Electrical impedance of muscle during isometric contraction. *Physiol Meas.* 2003; 24(1):213-34; Jackson V M, Trout S J, Cunnane T C. Regional variation in electrically-evoked contractions of rabbit isolated pulmonary artery. *Br J Pharmacol.* 2002; 137(4):488-496) Another explanation could be based on the fact that electroporation disturbs the osmotic balance of the cells and causes cell swelling which in turn can result in a decrease of the conductance. (Ivorra A, Miller L, Rubinsky B. Electrical impedance measurements during electroporation of rat liver and muscle. In: 13*th International Conference on Electrical Bioimpedance and the* 8*th Conference on Electrical Impedance Tomography.;* 2007: 130-133. Available at: http://dx.doi.org/10.1007/978-3-540-73841-1_36 [Accessed Oct. 21, 2008]) Nevertheless, we believe that such swelling cannot be manifested as fast as would be required here in order to explain the conductance decrease during the sequence, particularly in Groups 1 and 2 (sequence duration=1 second).

NTIRE is not the first method to address the challenge of VSMC ablation. Several alternative technologies have been studied, and some have become a common clinical practice for the treatment of post-angioplasty and in-stent restenosis. These technologies include: cryoplasty (Fava M, Loyola S, Polydorou A, et al. Cryoplasty for Femoropopliteal Arterial Disease: Late Angiographic Results of Initial Human Experience. *J Vasc Interv Radiol.* 2004; 15(11):1239-1243), brachytherapy (Leon M, Teirstein P, Moses J, et al. Localized Intracoronary Gamma-Radiation Therapy to Inhibit the Recurrence of Restenosis after Stenting. *N Engl J Med.* 2001; 344(4):250-256), photodynamic therapy (Waksman R, Leitch I, Roessler J, et al. Intracoronary photodynamic therapy reduces neointimal growth without suppressing re-endothelialisation in a porcine model. *Heart.* 2006; 92(8): 1138-1144), radiofrequency ablation (Taylor G W, Kay G N, Zheng X, Bishop S, Ideker R E. Pathological Effects of Extensive Radiofrequency Energy Applications in the Pulmonary Veins in Dogs. *Circulation.* 2000; 101(14):1736-1742), drug-eluting stents (Stone G, Ellis S, Cox D, et al. A Polymer-Based, Paclitaxel-Eluting Stent in Patients with Coronary Artery Disease. *N Engl J Med.* 2004; 350(3):221-231) and molecular-based therapies (Aubart F C, Sassi Y, Coulombe A, et al. RNA Interference Targeting STIM1 Suppresses Vascular Smooth Muscle Cell Proliferation and Neointima Formation in the Rat. *Mol Ther.* 2008. Available at: http://dx.doi.org/10.1038/mt.2008.291 [Accessed Jan. 6, 2009]).

However, delayed re-endothelialization (Cheneau E, John M, Fournadjiev J, et al. Time Course of Stent Endothelialization After Intravascular Radiation Therapy in Rabbit Iliac Arteries. *Circulation*. 2003; 107(16):2153-2158), economic impact (Weintraub W S. The Pathophysiology and Burden of Restenosis. The American Journal of Cardiology. 2007; 100(5, Supplement 1):S3-S9) and late in-stent thrombosis (Lagerqvist B, James S, Stenestrand U, et al. Long-Term Outcomes with Drug-Eluting Stents versus Bare-Metal Stents in Sweden. *N Engl J Med*. 2007; 356(10):1009-1019; Costa M A, Sabate M, van der Giessen W J, et al. Late Coronary Occlusion After Intracoronary Brachytherapy. *Circulation*. 1999; 100(8):789-792) are some of the major concerns with all of the current VSMC ablation modalities. We believe NTIRE should be further investigated as an alternative to current modalities, since it has two major advantages.

First, its non-pharmacological nature can overcome biological phenomena such as cellular adaptation or acquired drug-resistance, thus achieving higher local efficiency. The non pharmacologic nature also guarantees an accurate local effect that depends entirely on electric field distribution and does not induce collateral damage to adjacent structures.

Second, its ultra short duration can decrease intervention time in the clinical setting of primary percutaneous intervention (PCI). It enables one to minimize obstruction of blood flow to viable myocardial tissue during the ablation procedure. Moreover, short intervention duration will enable prompt and full endothelium recovery by immediate recruitment of circulating progenitor endothelial cells. Incomplete neointimal coverage has been demonstrated as a probable cause for late stent thrombosis in patients with drug-eluting stents6, as well as a reason for brachytherapy failure. (Waksman R, Bhargava B, Mintz G S, et al. Late total occlusion after intracoronary brachytherapy for patients with in-stent restenosis. *Journal of the American College of Cardiology*. 2000; 36(1):65-68)

The complete endothelial regeneration observed in this report can be attributed to two properties of NTIRE. First, the ultra short duration of the modality enabled immediate repopulation of the endothelium by either endothelial cells from adjacent non treated areas, or by adherence of progenitor endothelial cells from the circulation. Second, the non-thermal nature of this modality minimized the insult to extra cellular components of the endothelial layer, probably creating a more comfortable environment for cellular regeneration.

Endovascular NTIRE has clinical potential for both the prevention and the treatment of restenosis following angioplasty. Due to its short duration and high efficiency NTIRE can become a preventive treatment immediately before stent deployment. It might also prove to be a valuable tool for the effective treatment of in-stent restenosis several weeks following the angioplasty.

All animals were evaluated after a follow-up period of one week. This was based on our previous study, where ablation efficiency was evident by the complete loss of VSMC population as early as one week following NTIRE. (Maor E, Ivorra A, Leor J, Rubinsky B. The Effect of Irreversible Electroporation on Blood Vessels. *Technology in Cancer Research and Treatment*. 2007; 6(4):255-360).

CONCLUSION

This study provides scientific proof and justification irreversible electroporation as a promising non-thermal, non pharmacological, ultra short modality for the treatment of VSMC proliferation and the clinical problem of in-stent restenosis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A balloon catheter device for insertion into a vessel and reducing neointima, comprising:

a flexible elongated shaft comprising a distal end portion for insertion into a vessel;

a balloon positioned at the distal end portion;

a first electrode positioned at the distal end portion of the shaft, the first electrode being comprised of a conductive material which is flexible and generally conforms to an outer surface of the balloon during expansion of the balloon;

a second electrode positioned at a point relative to the first electrode so as to allow electrical current to flow between the first and second electrodes and through vascular tissue to the first electrode, the second electrode being comprised of a conductive material which is flexible and conforms to the outer surface of the balloon during expansion of the balloon;

wherein the first electrode and second electrode are positioned in an overlapping relationship on a single longitudinal axis to form a double helix spanning an entire length of the balloon, and comprising multiple helical turns around the balloon, and wherein the first and second electrodes are positioned to generate an electric field encompassing substantially the entire outer balloon surface; an electrical power source which provides electrical pulses to the electrodes for durations and in amounts sufficient to subject substantially all vascular cells in a target area of the vessel to non-thermal irreversible electroporation (NTIRE).

2. The device of claim 1, wherein the first and second electrodes are formed from electrically conductive ink drawn on the balloon.

3. The device of claim 1, wherein the device will carry out NTIRE using a voltage and a current with defined ranges over a defined period of time and in absence of drug being delivered into the vascular cells.

4. The device of claim 3, wherein the electrical power source is designed to emit pulses wherein the pulses have a duration of from 50 to 200 microseconds.

5. The device of claim 1, wherein the electrical power source applies current in pulses.

6. The device of claim 5, wherein the electrical power source is configured to apply pulses having a duration of from 50 to 200 microseconds.

7. The device of claim 6, wherein the electrical power source is configured to apply pulses of a current in a range of from 2,000 V/cm to 6,000 V/cm.

8. The device of claim 7, wherein the electrical power source is configured to apply between two and twenty-five pulses.

9. The device of claim 8, wherein the electrical power source is configured to apply 10 pulses for 100 microseconds each at a current of 3,800 V/cm.

* * * * *